United States Patent [19]

Draper et al.

[11] Patent Number: 5,248,670
[45] Date of Patent: Sep. 28, 1993

[54] ANTISENSE OLIGONUCLEOTIDES FOR INHIBITING HERPESVIRUSES

[75] Inventors: Kenneth G. Draper, San Marcos; David J. Ecker, Carlsbad; Christopher K. Mirabelli, Encinitas; Stanley T. Crooke, Carlsbad, all of Calif.

[73] Assignee: ISIS Pharmaceuticals, Inc., Carlsbad, Calif.

[21] Appl. No.: 485,297

[22] Filed: Feb. 26, 1990

[51] Int. Cl.$^5$ ............... A61K 31/70; C07H 21/00; C07H 21/02; C07H 21/04
[52] U.S. Cl. ......................... 514/44; 536/24.5
[58] Field of Search ............... 536/27; 435/6; 514/34; 935/78

[56] References Cited

U.S. PATENT DOCUMENTS

| | | | |
|---|---|---|---|
| 4,806,463 | 2/1989 | Goodchild et al. | 435/5 |
| 5,004,810 | 4/1991 | Draper | 536/27 |
| 5,110,802 | 5/1982 | Cantin et al. | 514/44 |
| 5,166,195 | 11/1992 | Ecker | 514/44 |

OTHER PUBLICATIONS

D. J. McGeoch et al.; J. Gen. Virol. 69, 1531–1574 (1988).
D. J. McGeoch, A. Dolan, S. Donald, F. Rixon, J. Mol. Biol. 181; 1–13 (1985).
D. J. McGeoch, A. Dolan, S. Donald and D. H. K. Brauer; Nucleic Acids Res. 14; 1727–1745 (1986).
L. J. Perry, D. J. McGeoch, J. Gen. Virol. 69: 2831–2846 (1988).
E. D. Blair, C. C. Blair, E. K. Wagner; J. Virol. 61: 2499–2508 (1987).
M. Ceruzzi, K. Draper; Nucleosides and Nucleotides 8: 815–818 (1989).
M. C. Frame, H. S. Marsden, B. M. Dutia; J. Gen. Virol. 66: 1581–1587 (1985).
M. Matsukura, K. Shinozuka, G. Zon, H. Mitsuya, M. Reitz, J. S. Cohen, S. Broder; Proc. Natl. Acad. Sci. USA 84: 7706–7710 (1987).
M. Kulka, C. Smith, L. Aurelian, R. Fishelevich, K. Meade, P. Miller, P.O.P. T'so; Proc. Natl. Acad. Sci. USA 86: 6868–6872 (1989).
C. Smith, L. Aurelian, M. Reddy, P. Miller, P.O.P. Ts'o, Proc. Natl Acad. Sci, USA 83, 2787–2792 (1986).
A. Davison, J. Scott; J. Gen. Virol 67: 1759–1816 (1987).
T. Kouzarides, A. Bankier, S. Satchwell, K. Weston, P. Tomlinson, B. Barrell; J. Virol. 61: 125–133 (1987).
R. Baer, A. Bankeir, M. Biggin, P. Deininger, P. Farrell, T. Gibson, G. Hatfull, G. Hudson, S. Satchwell, C. Sequin, P. Tuffnell, B. Barrell; Nature 310: 207–211 (1984).
G. Lawrence, M. Chee, M. Craxton, U. Gompels, R. Honess, B. Barrell; J. Virol. 64: 287–299 (1990).

*Primary Examiner*—Johnnie R. Brown
*Assistant Examiner*—Gary L. Kunz
*Attorney, Agent, or Firm*—Woodcock Washburn Kurtz Mackiewicz & Norris

[57] ABSTRACT

Antisense oligonucleotides are disclosed having a length of 15–30 nucleotides containing the CAT sequence and hybridizable to herpes simplex virus type I gene UL13, UL39, or UL40. These antisense oligomers inhibit the replication of the virus at least three-fold. Pharmaceutical compositions containing these oligonucleotides as the active ingredients are also disclosed.

4 Claims, 25 Drawing Sheets

Fig. 3A

```
base no.   1
HSV-1      ATGGATGAGT CCCGCAGACA GCGACCTGCT GGTCATGTGG CAGCTAACCT
HSV-2      ATGGATGAGT CCGGGCGACA GCGACCTGCT GGTCGTGTGG CAGCTGACAT
Matches    ATGGATGAGT CC-G--GACA GCGACCTGCT GGTC-TGTGG CAGCT-AC-T
                                                                 50

51
HSV-1      CAGCCCCCAA GGTGCACGCC AACGGTCCTT CAAGGATTGG CTCGCATCCT
HSV-2      CAGCCCCCAA GGTGCACACC GACGCTCCTT CAAGGCCTGG CTCGCGTCCT
Matches    CAGCCCCCAA GGTGCAC-CC -ACG-TCCTT CAAGG--TGG CTCGC-TCCT
                                                                 100

101
HSV-1      ACGTACACTC CAACCCCCAC GGGGCCTCCG GGGCCCCCAG CGGCCCCTCT
HSV-2      ACATACACTC CCTCAGCCGC CGGGCGTCCG CGGGCCCAAG CGGCCCCTCC
Matches    AC-TACACTC C---C--C-C -GGGC-TCCG -GGCCCC-AG CGGCCCCTC-
                                                                 150

151
HSV-1      CTCCAGGACG CGGCCGTCTC CCGCTCCTCC CACGGGTCCC GCCACCGATC
HSV-2      CCCCGAGACG GCGCGGTCTC CGGAGCCCGC CCCGGGTCCC GCCGCCGATC
Matches    C-CC--GACG -CGC-GTCTC C-G--CC--C C-CGGGTCCC GCC-CCGATC
                                                                 200

201
HSV-1      CGGCCTCCGC GAGCGGCTTC GCGCGGGACT ATCCCGATGG CGAATGAGCC
HSV-2      CAGCTTCCGG GAGCGGCTTC GCGCGGGACT GTCCCGATGG CGAGTGAGCC
Matches    C-GC-TCCG- GAGCGGCTTC GCGCGGGACT -TCCCGATGG CGA-TGAGCC
                                                                 250

251
HSV-1      GCTCGTCTCA TCGCCGCGCG TCCCCCGAGA CGCCCGGTAC GGCGGCCAAA
HSV-2      GCTCGTCTCG TCGCCGCTCG TCCCCCGAGG CCCCCGGCCC TGCGGCCAAG
Matches    GCTCGTCTC- TCGCCGC-CG TCCCCCGAG- C-CCCGG--C -GCGGCCAA-
                                                                 300
```

Fig. 3B

```
       301
HSV-1    CTGAACCGCC CGCCCCTGCG CAGATCCCAG GCGGCGTTAA CCGCACCCCC   350
HSV-2    CTAAGGCGCC CGCCCCTGCG CAGGTCCGAG ACGGCCATGA CCTCGCCCCC
Matches  CT-A--CGCC CGCCCCTGCG CAG-TCC-AG -CGGC--T-A CC-C-CCCCC 351
HSV-1    CTCGTCCCCC TCGCACATCC TCACCCTCAC GCGCATCCGC AAGCTATGCA   400
HSV-2    GTCGCCCCCC TCGCACATCC TGTCCCTCGC GCGCATCCAC AAGCTATGCA
Matches  -TCG-CCCCC TCGCACATCC T--CCCTC-C GCGCATCC-C AAGCTATGCA 401
HSV-1    GCCCCGTGTT CGCCATCAAC CCCGCCCTAC ACTACACGAC CCTCGAGATC   450
HSV-2    TCCCCGTATT CGCCGTCAAC CCCGCCCTCC GCTACACGAC CTCGGAGATC
Matches  -CCCCGT-TT CGCC-TCAAC CCCGCCCT-C -CTACACGAC C---GAGATC 451
HSV-1    CCCGGGGCCC GAAGCTTCGG GGGTCTGGG  GGATACGGTG ACGTCCAACT   500
HSV-2    CCCGGGGCCC GCAGCTTCGG GGGCTCGGGG GGTACGGCG  AGGTGCAGTT
Matches  CCCGGGGCCC G-AGCTTCGG GGG-TC-GGG GG-TACGG-G A-GT-CA--T 501
HSV-1    GATTCGCGAA CATAAGCTTG CCGTTAAGAC CATAAAGGAA AAGGAGTGGT   550
HSV-2    GATTCGCGAA CACAAACTCG CCGTGAAGAC CATCCGGGAA AAAGAGTGGT
Matches  GATTCGCGAA CA-AA-CT-G CCGT-AAGAC CAT--GGAA  AA-GAGTGGT 551
HSV-1    TTGCCGTTGA GCTCATCGCG ACCCTGTTGG TCGGGGAGTG CGTTCTACGC   600
HSV-2    TTGCCGTGGA GCTCGTCGCG ACCCTGCTCG TGGGGGAGTG CGCTCTTCGC
Matches  TTGCCGT-GA GCTC-TCGCG ACCCTG-T-G T-GGGGAGTG CG-TCT-CGC
```

Fig. 3C

```
         601
HSV-1    GCCGGCCCGCA CCCACAACAT CCCACGACAT CCGGGCTTC  ATCGGCCCCC TCGGGTTCTC
HSV-2    GGCGGCCCGCA CCCACGACAT CCGGGCTTT  ATCACCCCGC TCGGGTTCTC
Matches  G-CGGCCCGCA CCCAC-ACAT CCGGGCTT-  ATC-C-CC-C TCGGGTTCTC
                                                                       700
         651
HSV-1    GCTGCAACAA CGACAGATAG TGTTCCCCGC GTACGACATG GACCTCGGTA
HSV-2    GCTGCAGCAG CGCCAGATCG TGTTCCCCGC GTACGACATG GACCTCGGCA
Matches  GCTGCA-CA- CG-CAGAT-G TGTTCCCCGC GTACGACATG GACCTCGG-A
                                                                       750
         701
HSV-1    AGTATATCGG CCAACTGGCG TCCCTGCGCA CAACAAACCC CTCGGTCTCG
HSV-2    AGTACATCGG CCAGCTGGCG TCCCTGCGCG CGACCACCCC CTCCGTCGCG
Matches  AGTA-ATCGG CCA-CTGGCG TCCCTGCGC- C-AC-A-CCC CTC-GTC-CG
                                                                       800
         751
HSV-1    ACGGCCCTCC ACCAGTGCTT CACGGAGCTG GCCCGCGCCG TTGTGTTTTT
HSV-2    ACGGCCCTCC ACCACTGCTT CACAGACCTG GCGGCGCCG TGTGTTCCT
Matches  ACGGCCCTCC ACCA-TGCTT CAC-GA-CTG GC-CGCGCCG T-GTGTT--T
                                                                       850
         801
HSV-1    AAACACCACC TGCGGGATCA GCCACCTGGA TATCAAGTGC GCCAACATCC
HSV-2    GAACACCAGG TGCGGGATCA GCCACCTGGA CATCAAGTGC GCCAACGTCC
Matches  -AACACCA-- TGCGGGATCA GCCACCTGGA -ATCAAGTGC GCCAAC-TCC
                                                                       900
         851
HSV-1    TCGTCATGCT GCGGTCGGAC GCCGTCTCGC CCGGCGGGC CGTCCTCGCC
HSV-2    TCGTGATGCT GCGATCGGAC GCGGTGTCGC TCCGGCGGGC CGTCCTGGCC
Matches  TCGT-ATGCT GCG-TCGGAC GC-GT-TCGC TCCGGCGGGC CGTCCT-GCC
```

Fig. 3D

```
        901                                                              950
HSV-1   GACTTTAGCC TCGTCACCCT CAACTCCAAC TCCACGATCG CCCGGGGCA
HSV-2   GACTTTAGCC TGGTGACCCT GAACTCCAAC TCCACGATAT CCCGGGGCCA
Matches GACTTTAGCC T-GT-ACCCT -AACTCCAAC TCCACGAT-- CCCGGGG-CA 951                                                              1000
HSV-1   GTTTTGCCTC CAGGAGCCGG ACCTCAAGTC CCCCCGGATG TTTGGCATGC
HSV-2   GTTTTGCCTC CAGGAGCCGG ACCTCGAGTC CCCCCGGGGG TTTGGGATGC
Matches GTTTTGCCTC CAGGAGCCGG ACCTC-AGTC CCCCCGG--G TTTGG-ATGC 1001                                                             1050
HSV-1   CCACCGCCCT AACCACAGCC AACTTTCACA CCCTGGTGGG TCACGGGTAT
HSV-2   CCGCCGCCCT GACCACGGCC AACTTTCACA CTCTGGTGGG GCACGGGTAC
Matches CC-CCGCCCT -ACCAC-GCC AACTTTCACA C-CTGGTGGG -CACGGGTA- 1051                                                             1100
HSV-1   AACCAGCCCC CGGAGCTGTT GGTGAAATAC CTTAACAACG AACGGGCCGA
HSV-2   AACCAGCCAC CGGAGCTCTC GGTAAAGTAC CTCAACAACG AGCGGGCCGA
Matches AACCAGCC-C CGGAGCT-T- GGT-AA-TAC CT-AACAACG A-CGGGCCGA 1101                                                             1150
HSV-1   ATTACCAAC CACCGCCTGA AGCACGACGT CGGGTTAGCG GTTGACCTGT
HSV-2   GTTTAACAAC CGCCCCCTGA AGCACGACGT CGGGCTGGCG GTCGATCTCT
Matches -TTTA-CAAC C-CC-CCTGA AGCACGACGT CGGG-T-GCG GT-GA-CT-T 1151                                                             1200
HSV-1   ACGCCCTGGG CCAGACGCTG CTGGAGTTGG TGGTTAGCGT GTACGTCGCC
HSV-2   ACGCCCTGGG GCAGACGCTG CTGGAGCTGC TGGTTAGCGT GTACGTGGCC
Matches ACGCCCTGGG -CAGACGCTG CTGGAG-TG- TGGTTAGCGT GTACGT-GCC
```

```
         1201                                                          1250
HSV-1    CCGAGCCTGG  GCGTACCCGT  GACCCGGTTT  CCCGGTTACC  AGTATTTTAA
HSV-2    CCGAGCCTGG  GCGTCCCCGT  GACCCGCGTC  CCGGGCTACC  AGTACTTTAA
Matches  CCGAGCCTGG  GCGT-CCCGT  GACCCG---T-  CC-GG-TACC  AGTA-TTTAA
         1251                                                          1300
HSV-1    CAACCAGCTG  TCGCCCGACT  TCGCCCTGCC  CCTGCTCGCC  TATCGCTGCG
HSV-2    CAACCAGCTC  TCGCCCGACT  TTGCCGTGGC  CCTCCTCGCC  TATCGCCGCG
Matches  CAACCAGCT-  TCGCCCGACT  T-GCC-TGGC  CCT-CTCGCC  TATCGC-GCG
         1301                                                          1350
HSV-1    TGCTGCACCC  AGCCCTGTTT  GTCAACTCGG  CCGAGACCAA  CACCCACGGC
HSV-2    TTCTGCACCC  CGCCCTCTTT  GTCAACTCGG  CCGAGACCAA  CACCCACGGC
Matches  T-CTGCACCC  -GCCCT-TTT  GTCAACTCGG  CCGAGACCAA  CACCCACGGC
         1351                                                          1400
HSV-1    CTGGCGTATG  ACGTCCCAGA  GGGCATCCGG  CGCCACCTCC  GCAATCCCAA
HSV-2    CTGGCGTATG  ACGTGCCGGA  GGGCATCCGG  CGCCACCTTC  GCAATCCCAA
Matches  CTGGCGTATG  ACGT-CC-GA  GGGCATCCGG  CGCCACCT-C  GCAATCCCAA
```

*Fig. 3E*

```
        1401              1451              1501              1551
HSV-1   GATTCGGGCGC GCGTTTACGG ATCGGTGTAT AAATTACCAG CACACACACA
HSV-2   GATTCGGGCGC GCGTTCACGG AGCAGTGTAT AAATTACCAG CGCACGCACA
Matches GATTCGGGCGC GCGTT-ACGG A-C-GTGTAT AAATTACCAG C-CAC-CACA 1451                                          1500
HSV-1   AGGCGATACT GTCGTCGGTG GCGCTGCCTC CCGAGCTTAA GCCTCTCCTG
HSV-2   AGGCCGTCCT GTCGTCGGTG TCGCTGCCGC CCGAGCTGAG GCCGCTGCTG
Matches AGGC--T-CT GTCGTCGGTG -CGCTGCC--C CCGAGCT-A- GCC-CT-CTG 1501                                          1550
HSV-1   GTGCTGGTGT CCCGCCTGTG TCACACCAAC CCGTGCGCGC GGCACGCGCT
HSV-2   GTGCTGGTCT CCCGCCTCT  TCACGCCAAC CCGGCCGCGC GCCACTCTCT
Matches GTGCTGGT-T CCCGCCT-TG TCAC--CAAC CCG---CGCGC G-CAC-C--CT 1551
HSV-1   GTCGTGA
HSV-2   GTCGTGA
Matches GTCGTGA
```

*Fig. 3F*

```
HSV-1   1 ..TACCACAGGTGGGTGCTTTGGAAACTTGTCGGGTCGCCGTGCTCCTGTG  48
          ||||||||||||||||| |||||  ||||||||  ||||||||||||||
HSV-2   1 ACCACAACAGGTGGGTGCTTCGGGGACTTGACGGTCGCCACTCTCCTGCG  50

.         .         .         .         .
         49 AGC......TTGCGTCCCTCCCCGGTTTCCTTTGCGCTCCCGGCCTTCCGGA  93
            |||      ||||||||||||||||||| ||||||||||||||||||| ||
         51 AGCCCTCACGTCTTCGGTTCCTGTTGCGTTGCCTGTGCGTTCCGGCCGGT  100

.         .         .         .         .
         94 CCTGCTCTCGCCTATCTCTTTGGCTTCCGGTGATTGTTCGGTCAGGCAGCG  143
            |||||||||||||||| | ||||| |||||| |||||||||| |||||||
        101 GCTGTCCTGTCGACAGATTGTTGGC..GACTGCCCGGGTGATTCGTCGGCC  149

.         .         .         .         .
        144 GCCTTGTCGAATCTCGACCCCACCACTCGCCGAACTCGCCGACGTCCCCT  193
            |||||||||||| |||||| |                  |||||||||
        150 GGTGCGTCCCTTCGGTCGTACCGCCCCCGCCCCACGGGCCCGCCCG  199

.         .         .         .         .
        194 CTCGAGCCCGCCGAAACCCGCCGGTCTGTTGAA[ATG]GCC  243
            |  ||||||||||||  ||||| |||||| || ||| ||
        200 CTGTTTCCGTTCATCGCGTCCGAGCCACCTTGGTTCCA[ATG]GCC  249

.         .         .         .         .
        244 AGCCGCCCCAGCCGCATCCCTCCCGTCGAAGCGCCCCGGTTGGGGG  293
            |||||||||||||||||||||||||||||||||||||||
        250 AACCGCCCTGCCGCATCCCTGCCCGGAGCGGTCCTCCGTCCGAACG  299

.         .         .         .         .
        294 ACAGGAGGCCGGGGCCCCAGCGCCAGCCACCAGGGGAGGCCCGGGG  343
            |||||| ||||||||||||||||||||||||||||||
        300 ACAGGAACCCGGGAGCCCGAGGTCGCCCCTGG..........  335
```

*Fig.4A*

```
344  CCCCTCTCGCCCCAGGCCACCACGTGTACTGCCAGCGAGTCAATGGCGTG  393
     ||| ||||||| ||||| |||| |||||| |||||||| |||||||||||
336  .........CGGCGACCACGTGTTTTGCAGGAAAGTCAGCGGGCGTG    372

394  ATGGTGCTTTCCGACAAGACGCCCGGTCCGGTCCGCATCCTACCGCATCAGCGA  443
     ||||||||||||| |||   |||||||||| |||| ||| |||||||| ||||
373  ATGGTGCTTTCCAGCGATCCCCCCGGCGCCCCTACCGCATTAGCGA    422

444  TAGCAACTTTGTCCAATGTGGTTCCAACTGCACCATGATCATCGACGGAG  493
     ||| ||||||||| ||||| |||||||||| |||| ||| |||||||||
423  CAGCAGCTTTGTTCAATGCGCTCCAACTGCAGTATGATAATCGACGGAG  472

494  ACGTGGTGCGGGCGCCCCCAGGACCCCGGGCGCATCCCCCGCT  543
     ||||||||||||||||| ||||||| |||||||  ||||||
473  ACGTGGCGCGGGTCATTTGCGTGACCTGAGGGCGTACGTCCACCGGC  522

544  CCCTTCGTTGCGGTGACAAACATCGGAGAGCCGGCAGCGACGGGGACCGC  593
     ||||||||||| ||| |||||||| | ||| |||||||| |||||||||
523  GCCTTCGCGTCGGATCTCAAACGTCGCAGCGGCCGAACCGC  572

594  CGTCGTGTGGCATTCGGGGGAACCCCACGTCGCTCGGCGGAGCGTCTACCG  643
     ||||||||||| | ||||| |||| |||| |||| ||||| ||||| |||
573  CGTCGTGGCCGCTCGGGCGAACCTTCCGGCGACTACATCCGTGG    622
```

*Fig. 4B*

```
644  GTACCCAGAGACGGCC....GACGTCCCCACCGAGGCCCTTGGGGCCCC...  687
     ||||||||||||||||    |||||||||||   |||||||   ||
623  GGACCCAGAGACGTCCGGGGAGTTCCTCCACGGAACCCAAGGACCCCCGAA  672

688  ........CCTCCTCCTCCCCGCTTCACCCTGGGTGGGGCTGTTGTTC     728
             ||  |||   ||||  |||        ||||    |  |
673  CCCCAAGGACCCCCAGGCTGTCCCCGCTCCTCCCCCCTTCCATG         722

729  CTGTCGGCGACACGGCGCGCTCTGCGGTATTCGGGGAGGGGATC         778
     |||||||| |||||||||||||| ||  ||||| ||  ||
723  GGCCACGAGTGCTGCGCCCGTGCGCGATGCCAGGGCGCCGAGAAGG      772

779  CAGTCGGCCCCCGGAGTTCGTCTCGGACGACCGGTTCGTCCGATTCCGAC  828
     |||||||  |||  ||||   |  |||||| || || ||  |||||||
773  GGGCCACGAGTGCTGCGGAGTCATGGTCAGACGGTCAGACGGTCCGACTCGTCCGACTCCGAA  822

829  TCGGATGACTCGGA..........GGACACGGACTCGGAGAC         860
     |||  |||||||||          |    |  ||||||||
823  ACGGAGGACTCGGACTCCTCGGACGAGGATACGGCTCGGGTTCGGAGAC  872

861  GCTGTCACACGCCTCCCTCGGACGTGTCCGGGGCCACGTACGACGACG    910
     ||||||  ||   |||  |||||   |||   |||   ||||||
873  GCTGTCTCGATCCCTCTTCGATCTGCGGCCGCAGGGCGACTGACGACGATG  922

911  CCCTTGACTCCGATTCGTCATGGATGACTCCCTGCAGATAGATGGCCCC    960
     ||  ||||||||||  |||   |||  ||||  ||||||||||
923  ACAGGACTCCGACTCGTCGGTCGGACTCGGACTCGGACGACTCGGAGCCCGACGTTGTC  972
```

*Fig. 4C*

```
 961 GTGTGTCGCCCGTGGAGCAATGACACCGGCCCCTGATGTT..........  1002
     || |||||  |   |  || |||  ||
 973 GTTCGTCGCAGATGGAGGCGACGGCCCCTGCCCCGTGGCCTTTCCCAAGCC  1022

1003 ..........TGCCCGGGACCCCCCGGCCCCGGGGCCCCGACGCCG  1036
               ||||||| ||||| ||||||||||||||
1023 CCGGGGCCCCGGCGACTCCCCCGGAAACCCGGGGCCTGGGCCCCGGCACCG  1072

1037 GTGGTCCCTCAGCGGTAGACCCCACACGCGCCAGAGGCCAGAGGCCGGCGCT  1086
     ||||||| ||| ||  ||  ||| |   |                |
1073 GGCCGGGCTCCGACGGACCCCGGACCCGGCGGTC..........GGCCGACTCC  1113

1087 GGTCTTGCGGCCGATCCCGCCGTGGCCCGGGACGACGGGAGGGGCTTTC  1136
     ||   ||| ||||   ||| |||||| ||||||   ||| ||| ||
1114 GATTCCGGGCCCCACGCGCGCCCAGGCGGACGTGGCGCGGTTCT  1163

1137 GGACCCCCGGAGAACGGGCCACGGTCTCAGGCCTACCCCCTGG  1186
     ||||||  ||||||| |||| |||  |||||||||| |||
1164 GGACAGCCAGCCCACTGTGGGAACGGACCCCGCTACCCAGTCCCCCTAG  1213

1187 AACTCACGCCCGAGAACGGGAGGCCGTGGCGCTTTCTGGGAGATGCC  1236
     ||||||||||||||||||||||||  ||||| |||||||| ||||
1214 AACTCACGCCCGAGAACGGGAGGCGGTGGCGGTTTCTGGGGACGCC  1263

1237 GTGAACCGCGAACCCGCTCATGCTGGAGTACTTTGCCGGTGCGCCCG  1286
     ||||| ||||| |||||||||||||||||||| ||||||||| ||||
1264 GTCGACCGCGAGCCCGCTCATGCTGGAGTACTTCTGTCGGTGCGCCCG  1313
```

*Fig. 4D*

```
1287  CGAGGAAACCAAGCGGTGTCCCCCAGGACACATTCGGCAGCCCCCTCGCC  1336
      |||||| || ||||| ||||| ||||||| |  |||||||||    ||||
1314  CGAGGAGAGCAAGCGGCGTGCCCCCACGAACCTTCGGCAGCGCCCCCGCC  1363

1337  TCACGGAGGACGACTTTGGGCTTCTCAACTACGCGCTCGTGGAGATGCAG  1386
      |||||||||||||||||||| |||| |||| |||||||||||||||| |
1364  TCACGGAGGACGACTTTGGGCCTCCTGAACTACGCGCTCGAGATGCGA    1413

1387  CGCCTGTGTCTGGACGTTCCTCCGGTCCCCGGTCCCGCCGAACGCATACATGCCCTA  1436
      ||||||||||| ||| ||||  |||| ||||||  || |||| ||||||| ||||||
1414  CGCCTGTGCCTGGACCTTCCCCCCGGTCCCCGGT CCCCAACGCATACACGCCCTA   1463

1437  TTATCTCAGGGAGTATGTGACGCGGCTGGTCAACGGGTTCAAGCCGCTGG  1486
      | |||||||||||||||| |||||||||||||||||||||||  ||||||
1464  TCATCTCAGGGAGTATGCGACGCGGCTGGTTAACGCGGTTCAAACCCCTGG  1513

1487  TGAGCCGGTCCGCATCCGGCCCTTACCGCATCCTGGGGTTCTGGTGCACCTG  1536
      || ||||||||| ||| |||| ||  ||||||||||||||| |||| ||||
1514  TGCGGGGGTCCGCCATCCGGCCCTCTCCGTATCGCATCTGGGATTCTGGTTCACCTG  1563

1537  CGGATCCGGACCCGGGAGGCCTCCTTTGAGGAGTGGCTGCGATCCAAGGA  1586
      || |||||| |||||||||||||||| ||||||||||| |||||||||||
1564  CGCATCCCCGTACCCGGGAGGCCTCCTCTTTGAGGAATGATGCGCTCCAAGGA  1613

1587  AGTGCCCTGGATTTTGGCCTGACGGAAAGGCTTCGCGAGCACGAAGCCC  1636
      | ||||||||| |||||||| |||||||||||||||||||||||| |||
1614  GGTGGACCTGGACTTCGGGCTTGACGGAAAGGCTTCGCCGAACACGAGGCCC  1663
```

*Fig. 4E*

```
1637 AGCTGGTGATCCTGGCCCAGGCTCTCTGGACCATTACGACTGTCTGATCCAC 1686
     ||||  ||||||||||||||||||||||  ||| |||||||||||||||||
1664 AGCTAATGATCCTGGCCCAGGCCCCTGAACCCCTACGACTGTCTGATCCAC 1713

1687 AGCACACCGCACACGCTGGTCGAGCGGGGCTGCAATCGGCCCTGAAGTA 1736
     ||||  |||||| ||||| |||| |||||||||| ||||  ||||||||
1714 AGCACCCCGAACACGCTCGTCGTCGAGCGGGGCAGTCGGCGCTGAAGTA 1763

1737 TGAGGAGTTTTACCTAAAGCGTTTTGGCGGGCACTACATGGAGTCCGTCT 1786
     |  |||||||||||| ||||||| |||||||||||||||||||||||||
1764 CGAAGAGTTTTACCTCAAGCGCTTCAAGGCGGGCACTACATGGAGTCCGTCT 1813

1787 TCCAGATGCGCCACATCGCCGGCTTTTGGCCTGCCGGGCCACGCGC 1836
     ||||||||| |||||||||||   || ||||||||||||| |||||
1814 TCCAGATGCACCACATCGCCGGGTTCCTGGCCGTGCCGGGCGACCCGC 1863

1837 GGCATGCGCCACATCGCCCTGGGCGAGAGGGGTCGTGGTGGAAATGTT 1886
     ||||||||||||||||   ||||||||||||||||||||  ||||||
1864 GGCATGCGCCACATCGCCCCCTGGGGCGACAGGGGTCGTGGTGGGAAATGTT 1913

1887 CAAGTTCTTTTTCCACCGGCCCTCTACGACCACCAGATCGTACCGTCGACCC 1936
     ||||||| |||||||||||||| |||||||||||| |||| |||||||||
1914 CAAGTTTCTTTTTCCACCGCCCCTCTACGACCACCACCAGATCGTGCCGTCCACCC 1963

1937 CCGCCATGCTGAACCTGGGACCCGCAACTACTACACCTCCAGCTGCTAC 1986
     ||||||||||||||||| ||||| ||||||||||||||| |||||||||
1964 CCGCCATGCTGAACCTCGGAACCCGCAACTACTACACGTCCAGCTGCTAC 2013
```

Fig. 4F

```
1987  CTGGTAAACCCCCAGGCCACCACAAACAAGGCGACCCTGCGGGCCATCAC  2036
      ||||||||||||||||||||||||||||||||||||||||||||||||||
2014  CTGGTAAACCCCCAGGCCACCACTAACCAGGCCACCCTCCGGGCCATCAC  2063
                                                       .
2037  CAGCAACGTCAGTGCCATCCTCCGCCCCGCAACGGGGCATCGGGCTATGCG  2086
      ||||||||||||||||||||||||||||||||||||||||||||||||||
2064  CGGCAACGTGAGCGCCATCCTCCGCCCCCGCAACGGGGCATCGGGCTGTGCA  2113
                                                       .
2087  TGCAGGCGTTTAACGACTCGGCGCCCCGGGACCGCCAGCGTCATGCCCGCC  2136
      ||||||||||||||||||||||||||||||||||||||||||||||||||
2114  TGCAGGCGTTCAACGACGCCAGCGCCACCGCCAGCATCATGCCGGCC    2163
                                                       .
2137  CTCAAGGTCCTTGACTCGCTGGTGGCGCACAACAAAGAGAGCGCGCG    2186
      ||||||||||||||||||||||||||||||||||||||||||||||||||
2164  CTGAAGGTCCTGGACTCCCTGGTGGGGCGCACACAAACAGAGACACGCG   221
                                                       .
2187  TCCGACCGGCGCGTGCCGTGTACCTGGAGCCCGTGGCACCGACGTGCGGG  2236
      ||||||||||||||||||||||||||||||||||||||||||||||||||
2214  CCCACCGGGGCGTGGCGTGTACCTGGAACCCTGGCACCAGCGACGTTCGGG  2263
                                                       .
2237  CCGTGCTCCGGATGAAGGGGTCCTCCGCCGGCGAAGAGGCCCAGCGCTGC  2286
      ||||||||||||||||||||||||||||||||||||||||||||||||||
2264  CCGTGCTCAGAATGAAGGCGCCCCTCGCCGGCGAGGAGGCCCAGCGCTGC  2313
                                                       .
2287  GACAATATCTTCAGCGCCCTCTGGATGCCAGACCTGTTTTTCAAGCGCCT  2336
      ||||||||||||||||||||||||||||||||||||||||||||||||||
2314  GACAACATCTTCAGCGCCCTTCAGCGCCCTGGATGCCGGACCTGTTCTTCAAGCGCCT  2363
```

*Fig. 4G*

```
2337 GATTCGCCACCTGGACGGGCGAGAAGAACGTCACATGGACCCTGTTCGACC 2386
     ||||||||||||||||||||||||||||| ||||| |||||||||||||||
2364 GATCCGCCACCTGGACGGGCGAGAAAAACGTCACCTGGTCCCTGTTCGACC 2413

2387 GGGACACCAGCATGTCGCTCGCCGACTTTCACGGGGAGGAGTTCGAGAAG 2436
     ||||||||||||||||||||||||||||||||||||||||||||||||||
2414 GGGACACCAGCATGTCGCTCGCCGACTTTCACGGCGAGGAGTTCGAGAAG 2463

2437 CTCTACCACGCACCCTCGAGGTTCATGGGGTTCGGCGAGCAGATACCCATCCA 2486
     |||||||||||||||||||||||||   ||| |||||||||| |||| ||||| 
2464 CTGTACGAGCACCCTCGAGGCCATGGGGTTCGGCGAAACGATCCCCATCCA 2513

2487 GGAGCTGGCCTATGGCATTGTGCCGCAGTGCGCCCACGACCGGGAGCCCCT 2536
     |||| |||||| ||| | ||||| |  |||||||| |||||||  |  |||
2514 GGACCTGGCGTACGCCGTCGTGCCGCAGCGCGCCACCACCGGAAGCCCCT 2563

2537 TCGTCATGTTCAAAGACGCGGTGAACCGGCCACTACATCTACGACACCCAG 2586
     || |||||||| ||| ||  |||||| |||||||||||||||||||| |||
2564 TCATCATGTTTAAGGACGCGGTAAACCGGCCACTACATCTACGACACGCAA 2613

2587 GGGGCGGCCATCGCCGGCTCCAACCTCTGCACCGAGATCGTCCATCCGGC 2636
     ||||||||||| ||||||||||||||||||| |||||||||||||||||||
2614 GGGGCGGCCATTGCCGGCTCCAACCTCTGCACGGAGATCGTCCACCCGTC 2663

2637 CTCCAAGCGATCCAGTGGGTCTGCAACCTGGGAAGCGTGAATCTGGCCC 2686
     ||||||| ||||||| ||||||||||||||||| |||||||||||||||||
2664 CTCCAAACGCTCCAGCGGGTCTGCAACCTGGGCAGCGTGAATCTGGCCC 2713
```

*Fig. 4H*

```
2687  GATGCGTCTCCAGGCAGACGTTTGACTTTGGGCGGCTCCGGACGCCGTG  2736
      |||||||||||||||||||||||||  ||||  ||||  |||||||||
2714  GATGCGTCTCCCCGGCGGACGTTCGATTTTGGCATGCTCCGGACGCCGTG  2763

2737  CAGGGCGTGCGTGCTGATGGTGAACATCATGATCGACAGCACGCTACAACC  2786
      |||||||||||||||      ||  ||||||||||||| ||||| |||||
2764  CAGGGCGTGCGTGCTAATGGTTAATATATCATGATAGACAGCACGCTGCAGCC  2813

2787  CACGCCCCAGTGCACCCGGCAACGACAACCTGCGGTCCATGGAATCG  2836
      ||  |||||||||||||||||||||||||||||||||||||||  |
2814  GACGCCCCAGTGCGCGGCCCACGACAACCTGCGGTCCATGGCATTG  2863

2837  GCATGCAGGGCCTGCACACGGCCTGCCTGAAGCTGGGGCTGGATCTGGAG  2886
      |||||||||||||||||||||||||||||||||||||| |||||||||||
2864  GCATGCAGGGCCTGCACACGGCCTGCCTGAAGATGGGCCTGGATCTGGAG  2913

2887  TCTGCCGAATTTCAGGACCTGAACAAACACATCGCCGAGGTGATGCTGCT  2936
      |||  ||||||||||||||||||||||||||||||||||||||||||||||
2914  TCGGCCGAGTTCCGGGACCTGAACACACACATCGCCGAGGTGATGCTGCT  2963

2937  GTCGGCGATGAAGACCAACGCCAACGCCTGTGCGTTCCGGGGCCCGTCCCT  2986
      |||||||||||||||||||||||||||| ||||||||||||||||||||||
2964  CGCGGCCATGAAGACCAGTAACGCCTGTGTGCGTTCCGGGGGCCGTCCCT  3013

2987  TCAACCACTTTAAGCGCAGCATGTATCGCGGCCGCTTTCACTGGGAG  3036
      || ||||||||||||||||||||||| |||||||||||||||||||||
3014  TCAGCCACTTTAAGCGCAGCATGTACCGGGCCGCTTTCACTGGGAG  3063
```

*Fig. 4I*

```
3037 CGCTTTCCGACGCCCGGCCGGTACGAGGGCGAGTGGGAGATGCTACG 3086
     ||||||||| |||| ||||||||||||||||||||||||||||||||
3064 CGCTTTTCGAACGCCAGCCCGCGTACGAGGGCGAGTGGGAGATGCTACG 3113

3087 CCAGAGCATGATGAAACACGGCCTGCCAACAGCCAGTTTGTCGCGCTGA 3136
     |||||||||||||||||||||||||||||||||||||||||||||| |
3114 CCAGAGCATGATGAAACACGGCCTGCCAACAGCCAGTTCATCGCGCTCA 3163

3137 TGCCCACGCGCCTCGGGCGCAGATCTCGACGTCAGCGAGGGCTTTGCC 3186
     ||||||||||||||||||||||||||||||||||||||||||||||||
3164 TGCCCACGCGCCCGGCCGCAGATCTCGACGTCAGCGAGGGCTTTGCC 3213

3187 CCCCTGTTCACCAACCTGTTCAGCAAGGTGACCCGGACGGCGAGACGCT 3236
     |||||||||||||||||||||||||||||||||||| |||||||||||
3214 CCCCTGTTCACCAACCTGTTCAGCAAGGTGACCAGGGACGGCGAGACGCT 3263

3237 GCGCCCCAACACGCTCCTCCTGCTAAAGGAACTGGAACGCACGTTTAGCGGGA 3286
     ||||||||||||||||||| |||| |||||||||||||||||| ||||||||
3264 GCGCCCCAACACGCTCTTGCTGCGAAGGAACTCGAGCGCACGTTCGGCGGGA 3313

3287 AGCGGCTCCTGGAGGTGATGGACAGTCTCGACGCCAAGCAGTGGTCCGTG 3336
     ||||||||||||||||||||  |||||||||||||||||||||||| |||
3314 AGCGGCTCCTGGACGCGATGAACGACGGGCTCGAGGCCAAGCAGTGGTCTGTG 3363
```

*Fig. 4J*

```
3337 CCGCAGGCGCTCCCGTGCCTGGAGCCCACCCCCTCCGGCGATTCAA 3386
     || |||||||||| |||||||||||| |||||||||||| ||||||
3364 GCCCAGGCGCCCTGCCTGGACCCCACCCCCGCCCTCCGGGGTTCAA 3413

3387 GACCGCGTTTGACTACGACCAGAAGTTGCTGACCTGTGTGCGGACC 3436
     |||||| ||||||||||||| ||||| |||||||||||||| |||
3414 GACGGCCTTCGACTACGACCAGGAACTGCTGATCGACCTGTGCAGACC 3463

3437 GCGCCCCCTACGTCGACCATAGCCAATCCATGACCCTGTATGTCACGGAG 3486
     |||||||| |||| ||||| ||||||||||||||||||||||||| |||
3464 GCGCCCCCTATGTTGATCACAGCCAATCCATGACTCTGTATGTCACAGAG 3513

3487 AAGGCGGACGGGACCCCCTCCCAGCCTCCACCCCTGTCCGCCTTCTGGTCCA 3536
     ||||||||||||| |||||| |||| ||||||||||||||||||||||||
3514 AAGGCGGACGCGCTCCCCGCGCTCCCCCCTGTCCGCCTTCTGGTCCA 3563

3537 CGCATATAAGCGGGACTAAAAACAGGGATGTACTACTGCAAGGTTCGCA 3586
     |||||||||||||||| ||| ||||||||||||||||||||||||||
3564 CGCATATAAGCGCGGCCTGAAGACGGGATGTACTACTGCAAGGTTCGCA 3613

3587 AGGCGACCAACAGCGGGGTCTTTGGCGGACGACAACATTGTCTGCATG 3636
     ||||||||||||||||||     |||||||||||||||  |||| ||
3614 AGGCGACCAACAGCGGGGTTCGCCGGACGACAACATCGTCTGCACA 3663

3637 AGCTGCGCGCTGTGA 3651
     ||||||||||||| |
3664 AGCTGCGCGCTGTAA 3678
```

*Fig. 4K*

```
HSV-1    1 GTACTACTGCAAGGTTCGCAAGGCGACCAAACAGCGGGGTGTTCGCCGGCG   50
            ||||||||||||||||||||| ||||||||||||||||| |||||||||
HSV-2    1 ..ACTACTGCAAGGTTCGCAAGGCGACCAAACAGCGGGTCTTTGGCGGCG   48

HSV-1   51 ACGACAAACATGTCTCTGCACAAGCTGCGCGCTGTGTAAGCAACA...GCGCTC   97
            ||||||||||| ||||||||||                    ||||||
HSV-2   49 ACGACAAACATTGTCTGCAC..GGCTGCGGCGCTGTGTGACCGACAAACCCCCTC   97

HSV-1   98 CGATCGGGGTCAGGCGTCGCTCTCGGTCCCGCATATCG..........   135
            |||| |||||||||||| ||||||||
HSV-2   98 CGCGCCAGGCCCGCCGCCCACTGTGTGCCCGCTCCCACGCGCTCCCCGCT   147

HSV-1  136 .........CCATGGATCCCGCGTCTCCCCCGCGAGCACCGACCCCT   175
                    ||||| ||||||||||||||| ||||||  |||||||
HSV-2  148 GCCATGGATTCCGCGGCCCCAGCCCTCTCCCCGCGCTCTGACGGCCCATAC   197

HSV-1  176 AGATACCCACGCGGTCGGGCGGCCCGGATTCCGGTGTGCCCCA   225
            ||||||||||| |||||||||||||| |||||||| ||||||
HSV-2  198 GGGCCATAGCGCGACGGGCGGACCTAGACCTAGCCCCAGATTCCAAAGTGCCCCG   247

HSV-1  226 CCCCCGAGCGGTACTTCTACACCTCCCAGTGCCCCGACATCAACCACCTT   275
            |||||||||| |||||||||||||||||||||||||||||||||||| |
HSV-2  248 ACCCCGAGAGGTACTTCTACACCTCCCAGTGTCCGACATTAACCACCTG   297

HSV-1  276 CGCTCCCTCAGCATCCTGAACCGTGGAGACCGAGCTCGTGTTCGT   325
            |||||||||||||||||| ||||||||||||||||||||| |||
HSV-2  298 CGCTCCCTCAGCATCCTTAACCGCTGGAAACCGAGCTGTTTCGT   347
```

*Fig. 5A*

```
326 GGGGACGAGGAGGACGTCTCCAAGCTCTCCGAGGGCGAGCTCGGCTTCT 375
    ||| ||||||||||||||||||||||||||||||||||||||||||
348 GGGGACGAGGAGGACGTCTCCAAGCTTTCCGAGGGCGAGCTCAGCTTTT 397

376 ACCGCTTTCTGTTTGCCTTCCTGTCGGGGACGACCTGGTGACGGAA 425
    |||||||| ||| ||||| |||||||| ||||||||||| |||||
398 ACCGCTTCCTCTTCGCTTCTTCCCGTCGGCCGACGACCTGGTTACGGAA 447

426 AACCTGGGCGCGGCCCTCTCCGGCCCTCTTCGAACAGAAGGACATTCTTCACTA 475
    |||||||||||||||||||||||||| ||||| ||||||||||||| |||||
448 AACCTGGGCGCGGCCCTCTCCGGCCCTGTTTGAGCAGAAGGACATTCTCCACTA 497

476 CTACGTGGAGCAGGAATGCATCGAGTCGTCCACTCGCCGTCTACAACA 525
    ||||||||||||||||||||||||||||||||||||||||| ||||
498 CTACGTGGAGCAGGAATGCATCGAAGTCGCACACTCGCCGTGTACAACA 547

526 TCATCCAGCTCTGGTGCTCTCTTTCACAACAACGACCAGGCGCCGCCTAT 575
    ||||||||||||||| ||| |||||||||||||||||||||||||||
548 TCATCCAGCTCTGGTGCTTTTCCACAACAACGACCAGGCCCGCCGAGTAC 597

576 GTGGCCCGCACCATCAACCACCCGGCCATTCGCTCAAGGTGGACTGGCT 625
    |||| ||| ||||||||||||||||||||||||||||||||||||||
598 GTGGCCGGCACCATCAACCACCCGGCCATCCGCGCCAAGGTGGACTGGCT 647

626 GGAGGCGCGGGTGCGGGAATGCGACTCGATCCCGAGAAGTTCATCCTCA 675
    ||| ||||||||||||||||||||  ||| ||| |||||||||| |||
648 GGAAGCGCGGGTGCGGGAATGCGCCTTCCGTTCCGGAAAAGTTCATTCTCA 697
```

*Fig. 5B*

```
676  TGATCCTCATCGAGGGGTCTTTTTGCCGTCGTTCGCCTCGTTCGCCATCGCG  725
     |||||||||||||||||| |||||| |||||||| |||||||||||||||
698  TGATCCTCATCGAGGGCATCTTTTTGCCGCCTCGTTGCCGTTGCCGCCATCGCC  747

726  TACCTGCGCACCAACAACCCTCCTGCGGGTCACCTGCCAGTCGAACGACCT  775
     ||||| |||||||||||||| |||||||||||||||||||||| ||||||
748  TACCTTCGCACCAACAACCCTTCTGCGGGTCACCTGCCAGTCAAACGACCT  797

776  CATCAGCCGGACGAGGCCGTGCATACGACAGCCTCGTGCTACATCTACA  825
     ||||||||| |||||||||||||||||||||| |||||||| |||||||
798  CATCAGCCGGGACGAGGCCGTGCACACGACAGCCCTCGTGTTACATCTACA  847

826  ACAACTACCTCGGGGACCCAAGCCCGGGCGAGGCGGTGTACCGG  875
     ||||||||||| ||||| |||||||||||| |||||||||||||
848  ACAACTACCTGGGGGCCCCAAGCCCGGACCGCGGCGTGTACGGG  897

876  CTGTTTCGGGAGGCGGTGGATATCGAGATCGGGTTCATCGATCCCAGGC  925
     ||||| |||| |||||||||||||||||||| |||| ||||||||||||
898  CTGTTCCGGCCAGGCGGTCGAGATCGAGATCGGATTTATCCGATCCCAGGC  947

926  CCCGACGGACAGCTCTATCCTGAGTCCGGCCCTGGGCCCTGGGGCCATCGAGA  975
     ||||||||||||||| |||||||||||||||||||||||||||||||||
948  GCCGACGGACAGCAGCCATATCCTGAGCCCGGCCCTGGCGGCCATCGAAA  997

976  ACTACGTGCGATTCAGCGGCGATCGCCTGCTGGGCCCTGATCCATATGCAG  1025
     ||||||||||||||||||||||||||||| |||||||||||||||||||
998  ACTACGTGCGATTCAGCGGCGATCGCCTGTTGGGCCTTATCCACATGAAG  1047
```

*Fig. 5C*

```
1026 CCCCTGTATTCCGCCCCCGAGCGCCAGCTTTCCCCTCAGCCTCAT 1075
        ||| ||||||||  ||||||  ||||||||||| ||||||||||
1048 CCACTGTTTTCCGCCCCCGACGCCAGCTTTCCGCTGAGCCTCAT 1097

1076 GTCCACCGACAAACACACCAACTTCTTCGAGTGCCCAGCACCTCGTACG 1125
        ||||||||||||||||||| |||| |||||||| ||||||||| ||||
1098 GTCCACCGACAAACACACCAATTTTTTCGAGTGTCGCAGCACCTCCTACG 1147

1126 CCGGGGCCGTCGTCAACGATCTGTGA 1151
        ||||| ||||||||||||||||||||
1148 CCGGGGCGTCGTCAACGATCTGTGA 1173
```

*Fig. 5D*

| HSV-1 | | VZV | | EBV | |
|---|---|---|---|---|---|
| UL5 | (6133-3485) | 55 | (95996-98641) | BBLF4 | (114259-111830) |
| UL8 | (11478-9226) | 52 | (90493-92808) | BBRF1 | (114204-116045) |
| UL9 | (14261-11706) | 51 | (87881-90388) | BBRF2 | (116045-119137) |
| UL13 | (19504-17948) | 47 | (83168-84700) | BGLF4 | (123613-122325) |
| UL29 | (53053-49463) | 29 | (50857-54471) | BALF2 | (164770-161384) |
| UL30 | (53807-57514) | 28 | (50636-47052) | BALF5 | (156746-153701) |
| UL39 | (77444-80857) | 19 | (28845-26518) | BORF2 | (76407-78887) |
| UL40 | (80926-81948) | 18 | (26493-25573) | BaRF1 | (78900-79808) |
| UL42 | (84113-85579) | 16 | (23794-22568) | BMRF1 | (79899-81113) |
| UL52 | (100048-103224) | 6 | (8577-5326) | BSLF1 | (86879-84257) |

ANTISENSE OLIGONUCLEOTIDES FOR INHIBITING HERPESVIRUSES

FIELD OF THE INVENTION

This invention relates to therapies and diagnostics for herpesvirus infections. In particular, this invention relates to antisense oligonucleotide interactions with certain portions of herpesvirus RNA which have been found to lead to modulation of the activity of the RNA and, thus, to modulation of the effects of the viruses themselves.

BACKGROUND OF THE INVENTION

Approximately 500,000 new cases of genital herpes are reported each year, and it is estimated that 30 million Americans are affected by this currently incurable disease. Similarly, it is estimated that there is an annual incidence of 500,000 new cases of herpes simplex gingivostomatitis and at least 100 million Americans suffer from recurrent herpes labialis. Overall the prevalence of seropositive individuals in the general population is approximately 70-80%. Although recurrent herpes simplex virus infections are the most prevalent of all herpesvirus infections, there is a need to develop more specific forms of therapy for diseases such as herpes simplex encephalitis, keratoconjunctivitis, herpetic whitlow and disseminated herpes infections of neonates and immunocompromised hosts.

The incidence of encephalitis is low (one case in 250,000 individuals per year), yet with existing therapy, the mortality rate is as high as 40% and approximately 50% of the survivors are left with severe neurological sequelae. Ocular infections are neither rare nor trivial. They are usually caused by HSV-1 and are a leading cause of blindness in many countries of the world. Herpetic whitlow is an occupational hazard of nurses, dentists and physicians which begins with erythema and tenderness of the distal segments of the fingers and is followed by coalescence and enlargement of the vesicles. An accompanying lymphangitis and lymphadenopathy of the draining lymphatics is a common feature. Neonatal HSV infection is usually encountered as a consequence of a child being born through an infected birth canal. The incidence of the disease is approximately 1 in 10,000 births. Mortality in babies with limited infection can be as high as 20% while mortality of neonates from disseminated infection, even with current therapy, can approach 75% and many survivors have significant neurological impairment.

Currently, nucleoside analogs are clearly the preferred therapeutic agents for HSV infections. A number of pyrimidine deoxyribonucleoside compounds have a specific affinity for the virus-encoded thymidine (dCyd) kinase enzyme. The specificity of action of these compounds confines the phosphorylation and antiviral activity of these compounds to virus-infected cells. A number of drugs from this class, e.g. 5-iodo-dUrd (IDU), 5-trifluoro-methyl-dUrd (FMAU), 5-ethyl-dUrd (EDU), (E)-5-(2-bromovinyl)-dUrd (BVDU), 5-iodo-dCyd (IDC), and 5-trifluoromethyl-dUrd (TFT), are either in clinical use or likely to become available for clinical use in the near future. IDU is a moderately effective topical antiviral agent when applied to HSV gingivostomatitis and ocular stromal keratitis, however its use in controlled clinical studies of HSV encephalitis revealed a high toxicity associated with IDU treatment. Although the antiviral specificity of 5-arabinofuranosyl cytosine (Ara-C) wa initially promising, its clinical history has paralleled that of IDU. The clinical appearance of HSV strains which are deficient in their ability to synthesize the viral thymidine kinase has generated further concern over the future efficacy of this class of compounds.

The utility of a number of viral targets has been defined for anti-HSV compound development. Studies with thiosemicarbazone compounds have demonstrated that inhibition of the viral ribonucleotide reductase enzyme is an effective means of inhibiting replication of HSV in vitro. Further, a number of purine nucleosides which interfere with viral DNA replication have been approved for treatment of human HSV infections. 9-($\beta$-D-arabinofuranosyl) adenine (Ara-A) has been used for treatment of HSV-1 keratitis, HSV-1 encephalitis and neonatal herpes infections. Reports of clinical efficacy are contradictory and a major disadvantage for practical use is the extremely poor solubility of Ara-A in water. 9-(2-hydroxyethoxymethyl) guanine (Acyclovir, ACV) is of major interest. In humans, ACV has been used successfully in the therapy of localized and disseminated HSV infections. However there appear to be both the existence of drug-resistant viral mutants and negative results in double-blind studies of HSV-1 treatment with ACV. ACV, like Ara-A, is poorly soluble in water (0.2%) and this physical characteristic limits the application forms for ACV. The practical application of purine nucleoside analogs in an extended clinical situation suffers from their inherently efficient catabolism, which not only lowers the biological activity of the drug but also may result in the formation of toxic catabolites.

All of the effective anti-HSV compounds currently in use or clinical testing are nucleoside analogues. The efficacy of these compounds is diminished by their inherently poor solubility in aqueous solutions, rapid intracellular catabolism and high cellular toxicities. An additional caveat to the long-term use of any given nucleoside analogue is the recent detection of clinical isolates of HSV which are resistant to inhibition by nucleoside compounds which were being administered in clinical trials. Antiviral oligonucleotides offer the potential of better compound solubilities, lower cellular toxicities and less sensitivity to nucleotide point mutations in the target gene than those typical of the nucleoside analogues.

It is apparent that new routes to the diagnosis and therapy of herpesvirus infections are greatly desired. It is particularly desired to provide compositions and methods for therapy which are, at once, highly effective and possessed of no or only minor side effects. Thus, the provision of antisense oligonucleotide therapies for herpesvirus infections in accordance with this invention satisfies the long-felt need for such therapies.

OBJECTS OF THE INVENTION

It is a principal object of the invention to provide therapies for herpesvirus and related infections.

It is a further object of the invention to provide antisense oligonucleotides which are capable of inhibiting the function of RNA of herpesviruses and related viruses.

Yet another object is to secure means for diagnosis of herpesvirus infection.

These and other objects of this invention will become apparent from a review of the instant specification.

SUMMARY OF THE INVENTION

In accordance with the present invention, oligonucleotides and oligonucleotide analogs are provided which are specifically hybridizable with RNA or DNA deriving from a gene corresponding to one of the open reading frames UL5, UL8, UL9, UL13, UL29, UL30, UL39, UL40, UL42 AND UL52 of herpes simplex virus type 1. The oligonucleotide comprises nucleotide units sufficient in identity and number to effect such specific hybridization. It is preferred that the oligonucleotides or oligonucleotide analogs be specifically hybridizable with a translation initiation site and preferably that the oligonucleotide comprise a sequence CAT.

In accordance with preferred embodiments, the oligonucleotides and oligonucleotide analogs are designed to be specifically hybridizable with DNA or even more preferably, RNA from one of the species herpes simplex virus type 1 (HSV-1), herpes simplex virus type 2 (HSV-2), cytomegalovirus, human herpes virus 6, Epstein Barr virus (EBV) or varicella zoster virus (VZV). Such oligonucleotides and analogs are conveniently and desirably presented in a pharmaceutically acceptable carrier.

In accordance with other preferred embodiments, the oligonucleotides and oligonucleotide analogs are formulated such that at least some of the linking groups between nucleotide units of the oligonucleotide units comprise sulfur-containing species such as phosphorothioate moieties.

Other aspects of the invention are directed to methods for diagnostics and therapeutics of animals, especially humans, suspected of having a herpesvirus infection. Such methods comprise contacting either the animal or a body fluid of the animal with oligonucleotides or oligonucleotide analogs in accordance with the invention in order to inhibit the proliferation or effect of such infection, or to effect a diagnosis thereof.

Persons of ordinary skill in the art will recognize that the particular open reading frames described for herpes simplex virus type 1 find counterparts in the other viruses named. Thus each of herpes simplex virus type 1, cytomegalovirus, human herpes virus type 6, Epstein Barr virus and varicella zoster virus are believed to have many analogous open reading frames which code for proteins having similar functions. Accordingly, the present invention is directed to antisense oligonucleotide therapy where the oligonucleotides or oligonucleotide analogs are directed to any of the foregoing viruses, or indeed to any similar viruses which may become known hereafter, which have one or more of such analogous open reading frames. For convenience in connection with the present invention, all such viruses are denominated as herpesviruses.

BRIEF DESCRIPTION OF THE DRAWINGS

FIGS. 3A, 3B, 3C, 3D, 3E and 3F depict a comparison of the UL13 translational open reading frames (ORFs) of the HSV-1, strain 17 and HSV-2, strain HG52 mRNA species.

FIGS. 4A, 4B, 4C, 4D, 4E, 4F, 4G, 4H, 4I, 4J and 4K are sequence comparisons of the UL39 gene DNAs for HSV-1, strain 17 and HSV-2, strain 333 with the translation initiation codon highlighted at 238 of HSV-1.

FIGS. 5A, 5B, 5C and 5D are sequence comparisons of the UL40 gene DNAs for HSV-1, KOS strain and HSV-2, strain 333 with the translation initiation codon highlighted at 138 of HSV-1.

FIGS. 6A, 6B and 6C is tabulation of the homologous ORFS among HSV-1, VZV, and EBV as predicted from published DNA sequence data.

DETAILED DESCRIPTION OF THE INVENTION

Figure 1:
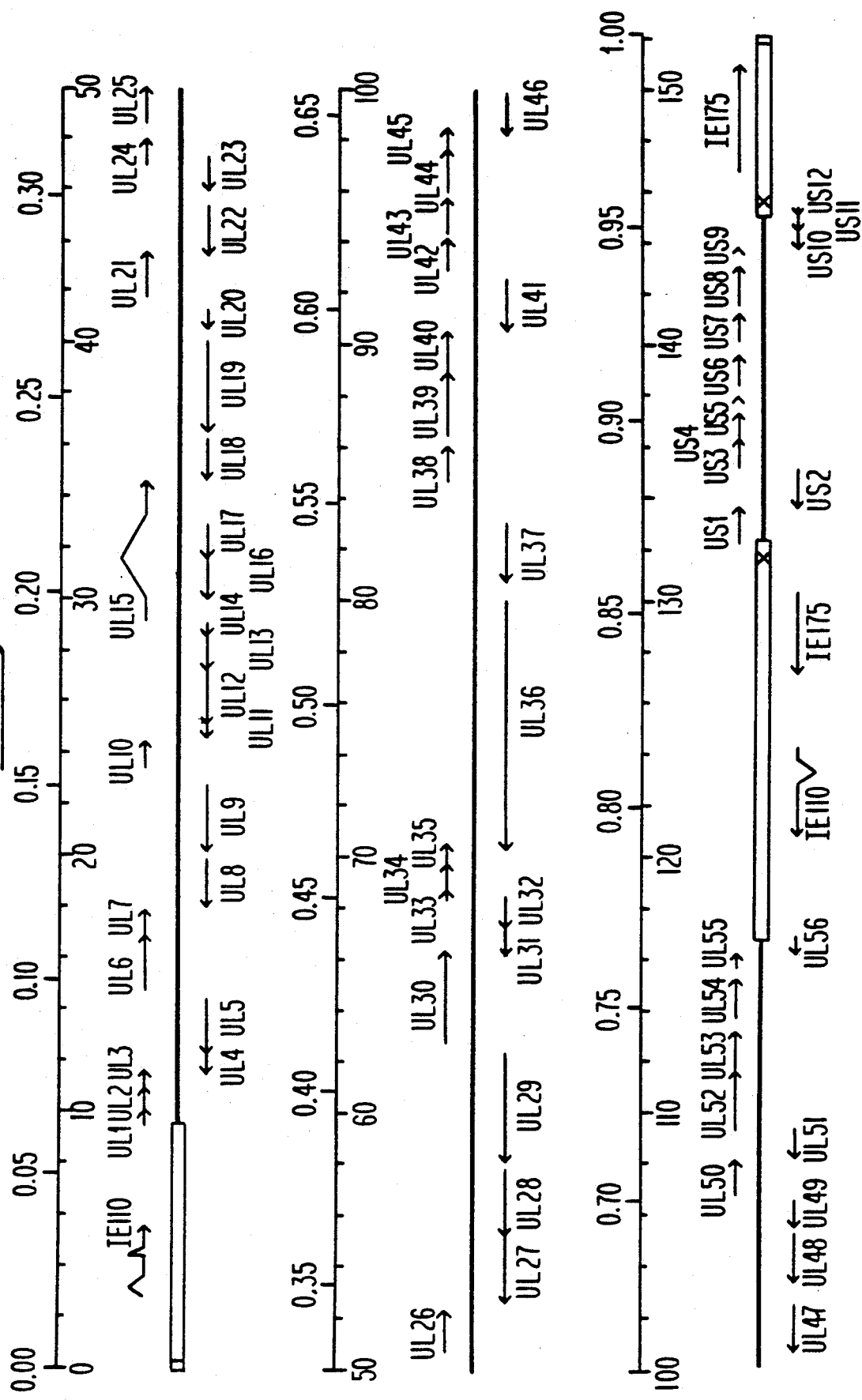
FIG. 1 is a depiction of the arrangement of the genes of herpes simplex virus type 1 in accordance with the data of McGeoch, D. J. et. al.; J. Gen. Virol. 69, 1531–1574 (1988).

Herpes simplex virus is the most studied of the human herpes viruses. The virus exists in two similar but distinct subtypes (HSV-1 and HSV-2); numerous strains of each subtype are known. Although the host range of some HSV strains is limited to certain tissues in vivo, the in vitro host range of all strains includes most human tissue types (both primary and transformed cells) as well as many non-human cells. The viral replication cycle is rapid, requiring approximately 24 h for HSV-1 and 48 h for HSV-2 to produce infectious progeny. The rapid replication and broad host range of HSV has resulted in an extensive molecular analysis of viral gene structure and of the control of viral gene expression during infection.

The productive infection of HSV consists of a number of differentiable stages which include: adsorption of the virus to the host cell membrane, fusion of the viral envelope with the cellular membrane, penetration of the non-enveloped virion to the nucleus of the cell, uncoating of viral nucleic acid, expression of viral genes and replication of the viral genome, nuclear packaging of the genome into newly formed viral capsids and finally, egress of the mature virion from the cell. Virally encoded proteins have been identified which control, in part, each of these stages of viral replication. The DNA sequence of the HSV-1 genome has been published and supports prior estimates that at least 71 unique viral proteins are encoded by the virus during a productive infection. McGeoch, D. J., Dolan, A., Donald, S., and Rixon, F. J. J. Mol. Biol. 181; 1–13 (1985); McGeoch, D. J., Dolan, A., Donald, S., and Brauer, D. H. K.; Nucleic Acids Res. 14: 1727–1745 (1986); McGeoch, D. J., Dalrymple, M. A., Davison, A. J., Dolan, A., Frame, M. C., McNab, D., Perry, L. J., Scott, J. E., and Taylor, P.; J. Gen. Virol. 69: 1531–1574 (1988); and Perry, L. J. and McGeoch, D. J.; J. Gen. Virol. 69: 2831–2846 (1988).

The structure of HSV genes is quite simple. The transcription of each mRNA is controlled by a promoter region located immediately 5' to the mRNA cap site for that gene. Splicing of mRNAs is rare and restricted primarily to the immediate early class of transcripts. A unique mRNA species exists for each putative protein product encoded by the virus and all of the viral mRNAs are considered to act like a monocistronic species even though multiple open reading frames (ORFs) are present in many of the mRNAs. The control of viral gene expression is a finely orchestrated cascade which can be divided into three general stages: the immediate early, early and late phases. The immediate early transcripts are synthesized at the onset of viral replication, even in the presence of translational inhibitors such as cycloheximide. Thus, the synthesis of this class of transcripts is controlled by existing cellular proteins and/or proteins brought into the cell by the infecting virion. The immediate early proteins are known to influence cellular and viral gene expression in both positive and negative manners, and the expression of these proteins is important for the transcriptional activation of other HSV genes, especially the early genes. The early gene transcripts encode many of the viral products which are necessary for replication of the viral genome. Because the synthesis of late gene transcripts is controlled by both the immediate early proteins and template abundance, the late genes are transcribed maximally only after viral DNA synthesis. The proteins encoded by the late genes include the envelope glycoproteins, the capsid proteins and other proteins which are necessary to maintain viral structure or permit egress of newly formed virions from the cell.

DNA sequence analysis predicts a conservative estimate of 71 proteins encoded within the HSV-1 genome. FIG. 1 sets forth nomenclature of HSV-1 gen s and genomic organization of the unique long (UL) and unique short (US) regions. Although a number of viral gene products have been shown to be dispensable to viral replication in vitro, only the viral thymidine kinase function has been known to be dispensable for viral growth in the human host. Logically, this leaves 70 gene targets which could be amenable to target-directed antiviral chemotherapy. During viral replication, the viral mRNAs represent the most diverse and versatile targets for antisense oligonucleotide inhibition.

Because the transcription of HSV mRNAs is tightly regulated within the cascade pattern of gene expression, the relative concentration of an HSV mRNA depends upon the time of sampling during the course of infection. Generally, maximal levels of mRNA concentration are reached at a time 3-4 hours after the onset of its synthesis. The rates of mRNA decay are not known for all of the HSV mRNAs; rates vary among the examples cited in the literature. A number of structural features of HSV mRNAs are important to the efficient translation of viral proteins. The 5' caps, consensus translation initiation codons and the 3' polyadenylated tails of HSV mRNAs are presumed to function in a manner analogous to similar mRNA structures which have been described for many cellular mRNAs. Splicing of HSV mRNAs is rare, but the splice sites of the immediate early transcripts represent another structural feature of the viral transcripts which could be considered as a feasible site of antisense inhibition. Additionally, unique structural features of the HSV UL48 mRNA have been reported to influence the rate of tegument protein synthesis. See Blair, E. D., Blair, C. C., and Wagner, E. K.; *J. Virol.* 61: 2499-2508 (1987). The presence of similar structures in other HSV mRNAs or the ability of these structures to influence synthesis of their cognate protein species has not been examined. Thus, a large number of potential structural regions of an HSV mRNA can be targeted as a putative site for antisense oligonucleotide inhibition of mRNA function. Indeed, the treatment of infected cells with oligonucleotides which are complementary to the splice sites of the US1 and US2 genes or the translation initiation region of the UL48 gene has resulted in the inhibition of HSV replication in vitro. See Smith, C. C., Aurelian, L., Reddy, M. P., Miller, P. S., and Ts'o, P. O. P.; *Proc. Natl. Acad. Sci. USA* 83: 2787-2792 (1986); and Ceruzzi, M, and Draper, K.; *Nucleosides and Nucleotides* 8: 815-818 (1989).

Viral gene products which are known to contribute a biological function to HSV replication can be categorized into three groups. These are 1. transcriptional activator or repressor proteins, 2. DNA replication proteins and 3. structural proteins. The immediate early class of HSV transcripts encode proteins which function as transcriptional activators and repressors of other viral genes. Strains of virus which are deficient in the production of these proteins have been reported and with the exception of the IE175 gene product, the immediate early proteins do not appear to be essential to viral replication. The transacting functions of other immediate early proteins can be substituted by either IE175 or host functions. The transcription of IE175 mRNA continues in the infected cell until levels of IE175 protein reach concentrations which inhibit the further transcription of IE175 mRNA. Thus, the inhibition of IE175 protein synthesis by an appropriate antisense oligonucleotide would result in steadily increasing levels of the IE175 mRNA, which could eventually exceed the molar threshold of concentration that represents the limit for effective oligonucleotide inhibition. An additional problem of antisense therapy designed for immediate early genes is that the temporal expression of the immediate early genes would necessitate a prophylactic administration of oligonucleotide for efficacy. Although this type of dosage is possible, it is not feasible in most human infections.

The most studied group of viral proteins are those involved in genomic replication. At least seven viral proteins (UL5, 8, 9, 29, 30, 42 and 52) are directly involved in viral DNA replication. The viral DNA polymerase, the thymidine kinase and the ribonucleotide reductase enzyme functions have been inhibited successfully with nucleoside analogues and work continues to find more potent versions of these compounds. The development of drug-resistant strains of HSV limit the feasibility of developing a nucleoside analogue with long-term efficacy in clinical use. Because the transcription of some late viral genes depends upon gene dosage for efficient expression, antisense inhibition of viral structural protein synthesis could also be accomplished indirectly by targeting the DNA synthetic proteins.

The use of structural proteins in antiviral efforts has centered on the development of vaccines and represents an unexplored field for chemotherapeutic intervention with antisense compounds. Proteins classed into this group include those known to play roles in viral assembly and structural integrity, viral adsorption, virion fusion with the host cell membrane and virus penetration into the infected cell.

Recently it has been reported that some viral proteins may serve bifunctional roles in HSV replication. In accordance with the present invention, these are now believed to offer the opportunity to directly affect multiple levels of viral replication by inhibiting a single protein product. The members of this class of viral proteins (UL13 and UL39) are limited in number, but represent targets which are believed to be very promising candidates for antisense inhibition. The viral proteins identified as the UL13 and UL39 ORFs of HSV-1 exhibit a high degree of nucleotide sequence conservation among homologues of various HSV-1 and HSV-2 subtypes. The UL13 and UL39 genes have now been determined to be the best sites for targeting therapeutic attack. A third protein, UL40, which forms the active ribonucleotide reductase enzyme complex with the UL39 protein, is also now believed to be a promising target for antisense inhibition.

Additional proteins are also believed to be good targets for antisense oligonucleotide therapeutic attack. These include proteins from the open reading frames UL5, UL8, UL9, UL29, UL30, UL42 And UL52. Accordingly, the present invention is preferably directed to inhibition of the function of mRNAs deriving from a gene corresponding to one of the open reading frames UL5, UL8, UL9, UL13, UL29, UL30, UL39, UL40, UL42 AND UL52 of herpes simplex virus type 1.

Figure 2A:
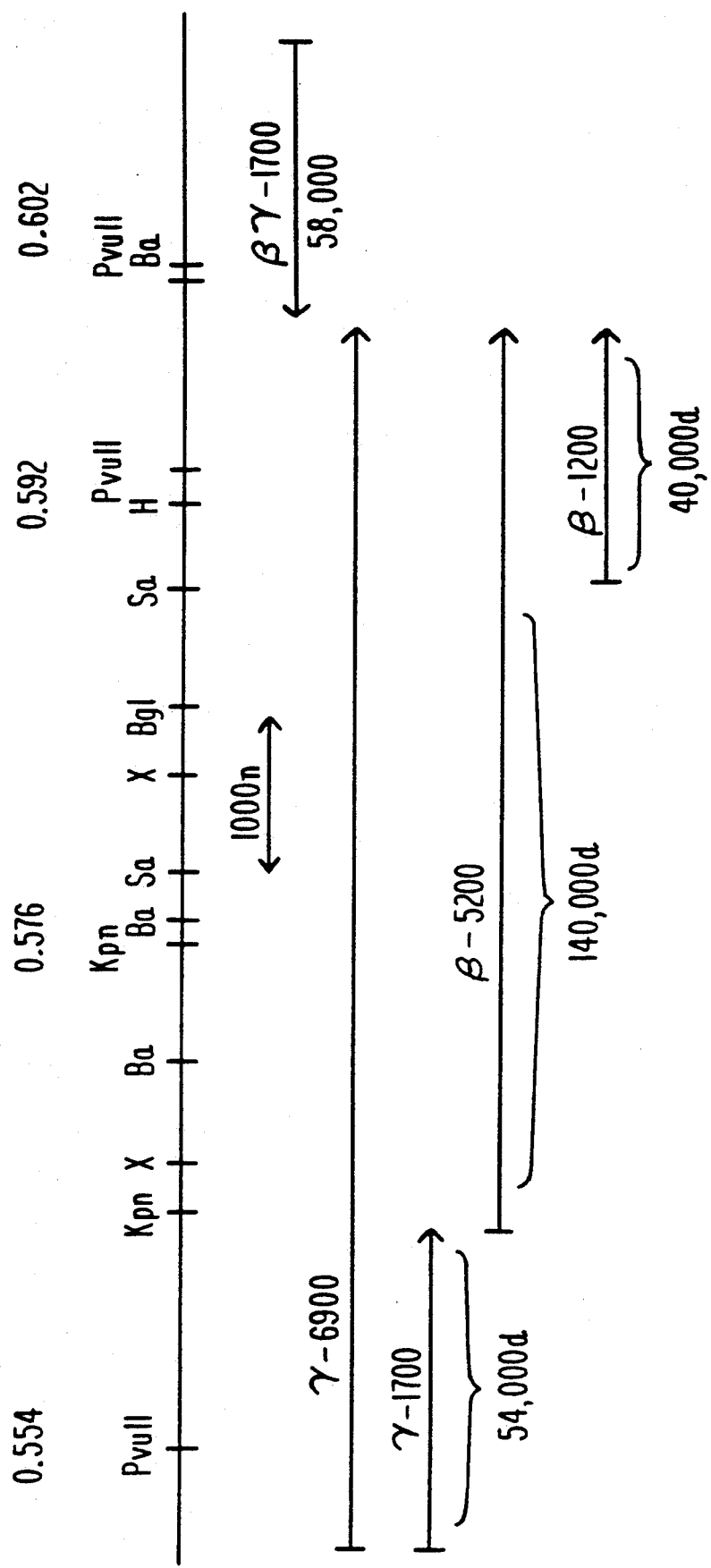
FIG. 2A reflects certain open reading frames (ORFs) including the ORFs for UL39 (140,000 d) and UL40 (40,000 d) in herpes simplex virus type 1.
Figure 2B:
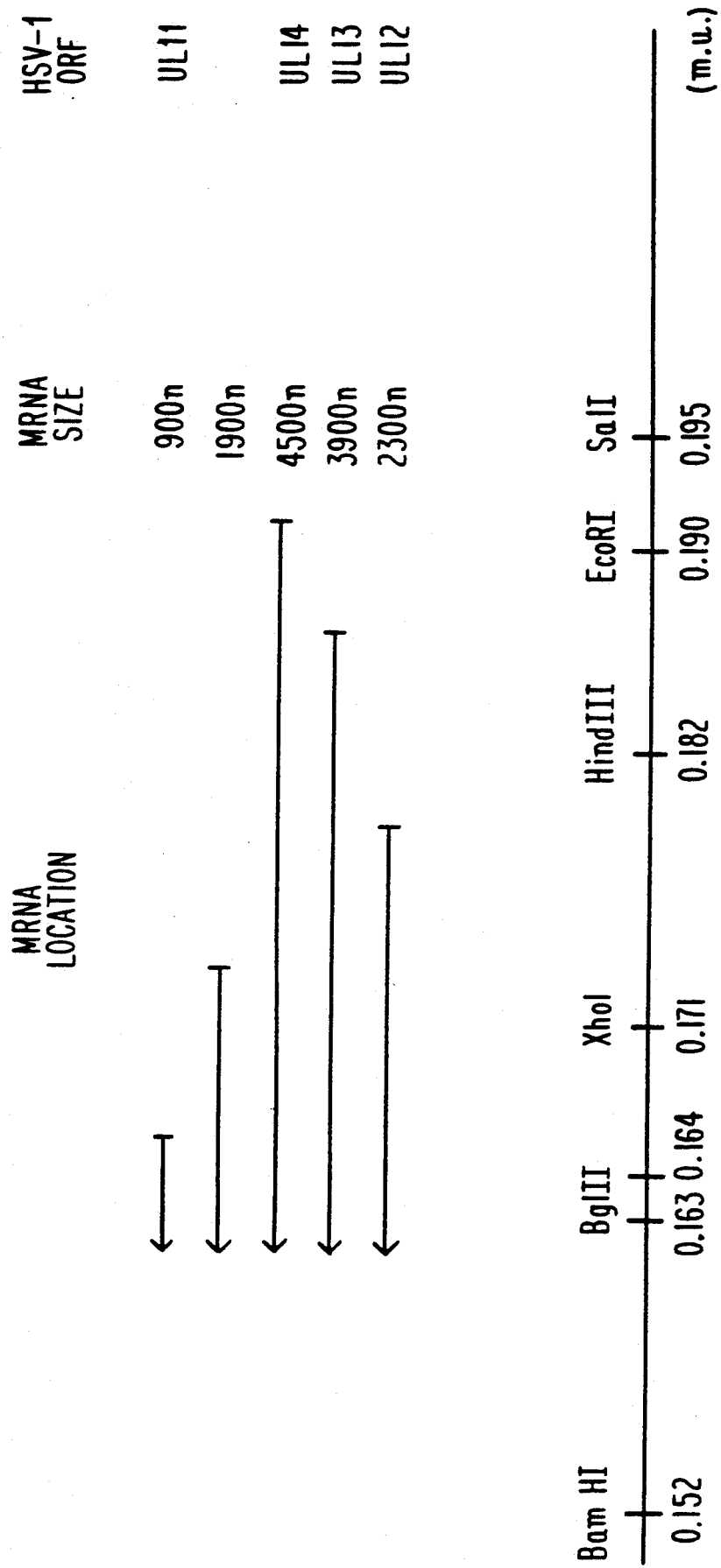
FIG. 2B shows one of a nested set of five 3'-coterminal transcripts including the UL13 gene of HSV 1, strain 17.

The UL13 protein of HSV-1 is a virion capsid protein which putatively encodes a protein kinase activity that is responsible for the specific phosphorylation of virion capsid proteins. The protein is encoded by a 4.1 kb mRNA which is one of a nested set of five 3'-coterminal transcripts as depicted in FIG. 2. The UL13 mRNA is a minor viral species which first appears at 3-4 hours after the onset of viral replication in tissue culture. The abundance of the UL13 mRNA increases somewhat after viral DNA replication occurs but remains low relative to the abundances of the major viral mRNAs throughout late times of infection. It has now been found through DNA sequence analysis that the mRNA sequence encoding UL13 is highly conserved among HSV-1 and HSV-2 isolates. The predicted molecular weights of the HSV-1 and HSV-2 proteins are 57193 and 57001, respectively. Because the synthesis of UL13 protein is not detected until after the onset of viral DNA synthesis, it is assumed that the primary control of UL13 translation is the abundance of the 4.1 kb mRNA. The role, if any, of the 5' non-translated region of the 4.1 kb mRNA in controlling the rate of UL13 protein synthesis has not been examined. A comparison of the translational open reading frames (ORFs) of the HSV-1 and HSV-2 mRNA species depicted in FIGS. 3A-3F reveal a conserved nucleotide sequence which is an attractive target for oligonucleotide inhibition of HSV UL13 synthesis and viral replication. The similarity in nucleotide sequence in this region (mismatches are only 205 of 1554 nucleotides) reflects an important structural feature of the mRNA which, it is now found, can be exploited by antisense oligonucleotide therapy to achieve broad antisense inhibitory activity against both HSV-1 and HSV-2 with single oligonucleotide sequences.

The UL39 protein of HSV-1 is closely associated with a second protein which is encoded by a neighboring gene, UL40, to form a complex that exhibits a ribonucleotide reductase activity. See Frame, M. C., Marsden, H. S., and Dutia, B. M.; *J. Gen. Virol.* 66: 1581-1587 (1985). A homologous set of proteins is encoded by HSV-2 and exhibits a similar ribonucleotide reductase activity. Alone, the HSV-2 homolog of the UL39 protein possesses an autophosphorylating protein kinase activity. A similar kinase activity has not been demonstrated for the HSV-1 UL39 protein. The UL39 and UL40 proteins are encoded by a pair of 3' coterminal mRNAs which are 5.2 and 1.2 kb in length, respectively. In an HSV-1 infection, the 5.2 kb mRNA is a major mRNA early in infection that decreases in abundance at late times of infection. The 1.2 kb mRNA becomes modestly abundant at early times and remains so throughout the infection. In an HSV-2 infection, the 1.2 kb mRNA homolog is the abundant early species and the 5.2 kb mRNA homolog is only moderately abundant. Again, both species of mRNA are only moderately abundant late in the infection. The biological significance of the differences in mRNA abundances between the HSV species is uncertain, but these differences may have profound effects upon the selection of an effective target for oligonucleotide inhibition of the viral ribonucleotide reductase or protein kinase activities. The proteins of the HSV ribonucleotide reductase complex are synthesized prior to viral DNA replication and the enzymatic activity probably plays an essential role in preparing substrates which are required for DNA synthesis. Inhibition of this important enzymatic function will not only interfere with DNA synthesis but also indirectly inhibit the synthesis of those late protein products whose encoding genes rely upon template abundance to efficiently synthesize the appropriate mRNAs. A comparison of the ORFs of the HSV ribonucleotide reductase mRNAs reveals a degree of nucleotide divergence, as shown in FIGS. 4A-4K, which may influence intertypic efficacy of the mRNA function. The divergence in nucleotide sequence around the AUG codons may require that separate nucleotide therapeutic preparations be used to inhibit the initiation of HSV-1 and HSV-2 UL39 and UL40 protein synthesis. Other regions within the body of the HSV-1 and HSV-2 UL39 and UL40 ORFs exhibit more extensive DNA homologies such that oligonucleotide preparations which have homologies to these regions may effectively inhibit replication of both HSV-1 and HSV-2.

The genome of HSV-1 contains both cis- and trans-acting elements which function in viral DNA replication. The cis-acting elements correspond to the origins of DNA replication and the trans-acting elements are the enzymes responsible for HSV-1 DNA replication. Seven of the open reading frames encoded by the HSV-1 genome correspond to the seven complementation groups known to be essential for HSV-1 DNA replication. These seven open reading frames encode the viral DNA polymerase enzyme (UL30), a single-stranded DNA binding protein (UL29), the ori$_S$-binding protein (UL9), a double-stranded DNA binding protein (UL42), and three proteins which comprise the helicase-primase complex (UL5, UL8 and UL52). The DNA sequence of these genes is known only for the HSV-1 genome, but the general colinearity and gross DNA sequence homologies between the HSV-1 and HSV-2 genomes in regions encoding critical viral functions has been established such that it is likely that an oligonucleotide inhibitor for each of these HSV-1 gene function will be found which will also inhibit functional expression of the homologous HSV-2 gene.

Three HSV gene targets have been reported to be sensitive to antisense inhibitors in in vitro assays. An oligonucleotide comprising a sequence of [dC]$_{28}$ linked internucleosidically by phosphorothioate groups inhibits HSV-2 DNA polymerase activity, but this action appears to be non-specific because the same oligonucleotide has been shown to interfere with genomic replication of an unrelated virus, Human Immunodeficiency virus. Cheng, Y-C., Gao, W., Stein, C. A., Cohen, J. S., Dutschman, G. E., and Hanes, R. N.; Abstract and poster presented at *Oligonucleotides as Antisense Inhibitors of Gene Expression: Therapeutic Implications*, held in Rockville, Md. (1989); Matsukura, M., Shinozuka, K., Zon, G., Mitsuya, H., Reitz, M., Cohen, J. S., and Broder, S.; *Proc. Natl. Acad. Sci. USA* 84: 7706-7710 (1987). Although this oligonucleotide has been shown to inhibit the respective viral replicases, inhibition of viral replication is not realized. Methylphosphonate linked and psoralen-derivitized oligonucleotides complementary to the splice junction acceptor sites of the HSV-1 US1 and US12 mRNAs have been shown to inhibit HSV-1 replication in vitro. Kulka, M., Smith. C. C., Aurelian, L., Fishelevich, R., Meade, K., Miller, P., and T'so, P. O. P.; *Proc. Natl. Acad. Sci. USA* 86: 6868-6872 (1989); and Smith, C. C., Aurelian, L., Reddy, M. P., Miller, P. S., and Ts'o, P. O. P.; *Proc. Nat'l Acad. Sci, USA* 83, 2787-2972 (1986). These results are intriguing because the target genes have been shown to be non-essential to HSV replication. An oligonucleotide sequence which is complementary to a gene which is essential to the replication of the virus is expected to be a better therapeutic agent than oligonucleotides targeted to non-essential gene products. Proof of this supposition was demonstrated by Ceruzzi and Draper using the HSV-1 UL48 mRNA as a target sequence. Ceruzzi, M, and Draper, K.; *Nucleosides and Nucleotides* 8: 815-818 (1989). The antiviral efficacy achieved by Ceruzzi and Draper with a natural (phosphodiester-linked) oligonucleotide was reported to be comparable to the efficacy observed by Smith et. al. using their modified oligonucleotides. This increase in antiviral efficacy was probably related to the important, but non-essential role of the UL48 protein in enhancing immediate early transcription of the virus.

The development of a set of oligonucleotide inhibitors of the UL13 capsid protein synthesis and virion protein phosphorylation represents a novel target for anti-HSV chemotherapy. The targeting of a number of independent viral functions offers the opportunity for broad intertypic antiviral activity by using the most highly effective antisense oligonucleotides determined by our studies in combination with each other or with an existing nucleoside therapy.

Comparison of the DNA sequences of herpes simplex virus type 1 (HSV-1), varicella zoster virus (VZV) and Epstein Barr Virus (EBV) has revealed that the genes which have now been found to be the best targets for antisense oligonucleotide attack are conserved among the human herpesviruses. The VZV and EBV genes which are homologous to the HSV-1 genes are set forth in FIG. 6. The predictions of ORFs are taken from GenBank annotations of published DNA sequences. Davison, A. J. & Scott, J. E., *J. gen. Virol.* 67: 1759-1816 (1987); McGeoch, D. J., Dalrymple, M. A., Davison, A. J., Dolan, A., Frame, M. C., McNab, D., Perry, L. J., Scott, J. E., & Taylor, P., *J. Gen. Virol.* 69: 1531-1574 (1988); Baer, R., Bankier, A. T., Biggin, M. D., Deininger, P. L., Farrell, P. J., Gibson, T. J., Hatfull, G., Hudson, G. S., Satchwell, S. C., Sequin, C., Tuffnell, P. S., & Barrell, B. G., *Nature* 310: 207-211 (1984).

Although the EBV BBRF2 and BORF2 genes are listed as being homologous to HSV-1 UL9 and UL39 genes, respectively, the encoded amino acids of these genes are not highly homologous. This lack of amino acid homology in the encoded ORFs may reflect a disruption of the EBV ORFs by splicing events within the mRNAs although verification of splices within these mRNAs has not yet been made. A number of regions of nucleotide homology which exist within these various herpesvirus genes are now believed to be good targets for antisense oligonucleotide inhibition. It is believed that an oligonucleotide which inhibits HSV-1 and/or HSV-2 and also possesses homology to the corresponding nucleotide sequence of either VZV or EBV will be an effective inhibitor of VZV and/or EBV replication as well. The sequence of the other human herpesviruses has not been published in toto, but limited nucleotide data available has shown that Human Cytomegalovirus (HCMV) and Human Herpesvirus 6 (HHV 6) have homology to the HSV-1 UL13 gene. Lawrence, G. L., Chee, M., Craxton, M. A., Gompels, U. A., Honess, R. W., and Barrell, B. G.; *J. Virol.* 64: 287-299 (1989). Additionally, the DNA sequence of the HCMV homolog of the HSV-1 UL30 gene has been published (Kouzarides, T., Bankier, A. T., Satchwell, S. C., Weston, K., Tomlinson, P., and Barrell, B. G.; *J. Virol.* 61: 125-133 (1987) and shown to exhibit regions of homology to the HSV-1 gene. Once the sequences of other human herpesviruses are known, it is believed that the genes which have now been targeted will be retained at least in part and show significant nucleotide homology to the original HSV gene sequences. The present invention employs oligonucleotides and oligonucleotide analogs for use in antisense inhibition of the function of messenger RNAs of herpesviruses. In the context of this invention, the term "oligonucleotide" refers to a plurality of joined nucleotide units formed from naturally-occurring bases and cyclofuranosyl groups joined by native phosphodiester bonds. This term effectively refers to naturally-occurring species or synthetic species formed from naturally-occurring subunits.

"Oligonucleotide analog," as that term is used in connection with this invention, refers to moieties which function similarly to oligonucleotides but which have non naturally-occurring portions. Thus, oligonucleotide analogs may have altered sugar moieties or inter-sugar linkages. Exemplary among these are the phosphorothioate and other sulfur containing species which are known for use in the art. They may also comprise altered base units or other modifications consistent with the spirit of this invention.

In accordance with certain preferred embodiments, at least some of the phosphodiester bonds of the oligonucleotide have been substituted with a structure which functions to enhance the ability of the compositions to penetrate into the region of cells where the RNA whose activity is to be modulated is located. It is preferred that such linkages be sulfur-containing. It is presently preferred that such substitutions comprise phosphorothioate bonds. Others such as alkyl phosphorothioate bonds, N-alkyl phosphoramidates, phosphorodithioates, alkyl phosphonates, and short chain alkyl or cycloalkyl structures may also be useful. In accordance with other preferred embodiments, the phosphodiester bonds are substituted with structures which are, at once, substantially non-ionic and non-chiral. Persons of ordinary skill in the art will be able to select other linkages for use in the practice of the invention.

Oligonucleotide analogs may also include species which include at least some modified base forms. Thus, purines and pyrimidines other than those normally found in nature may be so employed. Similarly, modifications on the cyclofuranose portions of the nucleotide subunits may also occur as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to hybridize with messenger RNA of herpesvirus or related viruses to inhibit the function of that RNA.

The oligonucleotides and oligonucleotide analogs in accordance with this invention preferably comprise from about 3 to about 50 subunits. It is more preferred that such oligonucleotides and analogs comprise from about 8 to about 25 subunits and still more preferred to have from about 10 to about 20 subunits. As will be appreciated, a subunit is a base and sugar combination suitably bound to adjacent subunits through phosphodiester or other bonds.

The oligonucleotides and oligonucleotide analogs of this invention are designed to be hybridizable with messenger RNA of herpesvirus. Such hybridization, when accomplished, interferes with the normal function of the messenger RNA to cause a loss of its utility to the virus. The functions of messenger RNA to be interfered with include all vital functions such as translocation of the RNA to the situs for protein translation, actual translation of protein from the RNA, and possibly even independent catalytic activity which may be engaged in by the RNA. The overall effect of such interference with the RNA function is to cause the herpesvirus to lose the benefit of the RNA and, overall, to experience interference with expression of the viral genome. Such interference is generally fatal to the virus.

In accordance with the present invention, it is preferred to provide oligonucleotides and oligonucleotide analogs designed to interfere with messenger RNAs determined to be of enhanced metabolic significance to the virus as described above. It has been found to be preferred to target one or more translation initiation portions of an open reading frame for antisense attack. As will be appreciated, such portions generally comprise the sequence AUG (in RNA) such that the oligonucleotide sequence CAT will be specifically hybridizable therewith. Accordingly, oligonucleotides and oligonucleotide analogs comprising the CAT sequence are preferred for these embodiments. Additional nucleotide subunits are preferably included in the oligonucleotide or oligonucleotide analog such that specific hybridization with the nucleic acid is attained to a high degree. Accordingly a number of subunits on one or either "side" of the CAT sequence which are designed to be complementary to the sequence adjacent to the translation initiation site to be hybridized with are included in the preferred oligonucleotides or analogs. Six to twelve subunits so adjacent on either "side" are convenient and are presently preferred, however larger or smaller numbers may be profitably employed without deviating from the spirit of this invention.

The oligonucleotides and oligonucleotide analogs of this invention can be used in diagnostics, therapeutics and as research reagents and kits. For therapeutic use, the oligonucleotide or oligonucleotide analog is administered to an animal, especially a human, suffering from a herpesvirus infection such as genital herpes, herpes simplex gingivostomatitis, herpes labialis, herpes simplex encephalitis, keratoconjunctivitis, herpetic whitlow or disseminated herpes infections of neonates and immunocompromised hosts.

It is generally preferred to apply the therapeutic agent in accordance with this invention topically or intralesionally. Other forms of administration, such as orally, transdermally, intravenously or intramuscularly may also be useful. Inclusion in suppositories may also be useful. Use of the oligonucleotides and oligonucleotide analogs of this invention in prophylaxis is also likely to be useful. Such may be accomplished, for example, by providing the medicament as a coating in gloves, condoms and the like. Use of pharmacologically acceptable carriers is also preferred for some embodiments.

The present invention is also useful in diagnostics and in research. Since the oligonucleotides and oligonucleotide analogs of this invention hybridize to herpesvirus, sandwich and other assays can easily be constructed to exploit this fact. Provision of means for detecting hybridization of oligonucleotide or analog with herpesvirus present in a sample suspected of containing it can routinely be accomplished. Such provision may include enzyme conjugation, radiolabelling or any other suitable detection systems. Kits for detecting the presence or absence of herpesvirus may also be prepared.

EXAMPLES

Cells and virus. HeLa (ATCC #CCL2) and Vero (ATCC #CCL81) cells used were obtained from the American Tissue Culture Collection. Cultures of HeLa cells were grown in Dulbecco's Modified Essential Medium (D-MEM) supplemented with 10% fetal bovine serum (FBS), penicillin (100 units/ml), streptomycin (100 micrograms/ml), and L-glutamine (2 mM). Cultures of Vero cells were grown in D-MEM supplemented with 5% FBS, penicillin, streptomycin and L-glutamine. Stock cultures of HSV-1 (strain KOS) and HSV-2 (strain HG52) were grown in Vero cells using low multiplicity infections (multiplicity of infection [MOI]=0.02 plaque forming units[PFU]/cell).

To assess the ability of oligonucleotides to inhibit HSV replication, an infectious yield assay was employed. HeLa cells were seeded at a density of $5 \times 10^5$ cells per well in Falcon 6 well tissue culture plates. Cells were overlaid with 3 ml of medium (D-MEM with 10% FBS) and incubated at 37° C. for 18–24 hr. Where appropriate, cells were overlaid with oligonucleotide preparations in 1 ml of culture medium at 24 hr after seeding the plates. Following an 18 hr incubation, all wells were rinsed with phosphate buffered saline and infected with either HSV-1 or HSV-2 at varying multiplicities of infection (MOI) suspended in 0.5 ml of serum-free D-MEM. Virus and cells were incubated at 37° C. for 1 hr with occasional rocking. Following viral adsorption, unadsorbed virus was rinsed away by washing the cells with phosphate buffered saline. Where appropriate, 1 ml of medium (D-MEM with 10% FBS) containing 4 µM concentrations of oligonucleotide were added to the well and the cells were incubated for 48 hr at 37° C. Again, control wells received 1 ml of medium which contained no oligonucleotide.

The oligonucleotides used were designed to interfere with translation of either UL13, UL39 or UL40 mRNAs at a translation initiation region. They were synthesized on an Applied Biosystems 380B DNA synthesizer in accordance with the hydrogen phosphonate chemistry protocol to produce phosphorothioate oligonucleotide analogs. Phosphoramidate chemistry protocols were used to produce conventional oligonucleotides having normal, phosphodiester bonds. The sequences prepared were as follows:

TABLE 1

| GENE HSV TYPE | OLIGONUCLEOTIDE SEQUENCE 5' | | | | | 3' | | NORMAL STRUCTURE CODE # | PHOSPHORO-THIOATE CODE # |
|---|---|---|---|---|---|---|---|---|---|
| UL48 1 | GTC | CGC | GTC | CAT | GTC | GGC | | 01 | 37 |
| UL13 1 | GGA | CTC | ATC | CAT | CCT | TCG | GCC | 02 | 34 |
| UL39 1 | GCG | GCT | GGC | CAT | TTC | AAC | AGA | 03 | 35 |
| UL40 1 | CGC | GGA | ATC | CAT | GGC | AGC | AGG | 04 | 36 |
| UL13 1 | ACC | GAG | GTC | CAT | GTC | GTA | CGC | 05 | 38 |
| UL13 2 | GGA | CTC | ATC | CAT | CCG | TCC | GCC | 06 | 39 |
| UL13 2 | GCC | GAG | GTC | CAT | GTC | GTA | CGC | 07 | 40 |
| UL39 2 | GCG | GTT | GGC | CAT | TGG | AAC | CAA | 08 | 41 |
| UL40 2 | GGC | GGG | ATC | CAT | GGC | GAT | ATG | 09 | 42 |

Virus was harvested into the overlay medium and triplicate wells of each experimental point were combined and standardized to a volume of 3 ml. The suspension was frozen and thawed four times, then drawn through a 20 gauge needle four times and stored at $-80°$ C. in 2 ml aliquots. Virus titer was determined by plaque assay on Vero cell monolayers. Dilutions of each virus preparation were prepared and duplicate aliquots of each dilution were adsorbed onto Vero cells for 1 hr with occasional rocking. After adsorption, the virus inoculum was removed by rinsing the plates with phosphate buffered saline and the cells were overlaid with 2 ml of D-MEM containing 5% FBS and 0.75% methyl cellulose. Cells were incubated at $37°$ C. for 72 hr before plaques were fixed with formalin, stained with crystal violet and counted. Plaque counts from treated wells were compared to those from the control wells to establish the degree of inhibition of virus replication.

Table 2 sets forth the data collected. The virus type, HSV-1 or HSV-2 and multiplicity of infection, MOI, are set forth. Inhibition of replication may be seen through comparison of experimental and control values.

TABLE 2

| Virus Type | MOI | Oligo. | Yield 1 | Yield 2 | Average | | % of control |
|---|---|---|---|---|---|---|---|
| HSV-1 | 0.5 | none | 5.4E+08 | 6.2E+08 | 5.80E+08 | $5.80 \times 10^8$ | 100.0 |
| HSV-1 | 0.5 | 01 | 6.3E+08 | 7.0E+08 | 6.65E+08 | $6.65 \times 10^8$ | 114.7 |
| HSV-1 | 0.5 | 03 | 7.7E+08 | 8.0E+08 | 7.85E+08 | $7.85 \times 10^8$ | 135.3 |
| HSV-1 | 0.5 | 04 | 3.9E+08 | 5.7E+08 | 4.80E+08 | $4.80 \times 10^8$ | 82.8 |
| HSV-1 | 0.5 | 05 | 7.7E+08 | 9.3E+08 | 8.50E+08 | $8.50 \times 10^8$ | 146.6 |
| HSV-1 | 0.5 | 08 | 7.9E+08 | 8.9E+08 | 8.40E+08 | $8.40 \times 10^8$ | 144.8 |
| HSV-1 | 0.5 | 42 | 5.7E+07 | 7.5E+07 | 6.60E+07 | $6.60 \times 10^7$ | 11.4 |
| HSV-1 | 0.5 | 39 | 1.4E+06 | 1.7E+06 | 1.55E+06 | $1.55 \times 10^6$ | 0.2 |
| HSV-1 | 0.5 | 41 | 1.2E+06 | 2.6E+06 | 1.90E+06 | $1.90 \times 10^6$ | 0.3 |
| HSV-2 | 0.5 | none | 8.0E+07 | 9.1E+07 | 8.55E+07 | $8.55 \times 10^7$ | 100.0 |
| HSV-2 | 0.5 | 01 | 7.6E+07 | 8.5E+07 | 8.05E+07 | $8.05 \times 10^7$ | 94.2 |
| HSV-2 | 0.5 | 03 | 8.3E+07 | 9.5E+07 | 8.90E+07 | $8.90 \times 10^7$ | 104.1 |
| HSV-2 | 0.5 | 04 | 4.9E+07 | 6.3E+07 | 5.60E+07 | $5.60 \times 10^7$ | 65.5 |
| HSV-2 | 0.5 | 05 | 6.6E+07 | 7.5E+07 | 7.05E+07 | $7.05 \times 10^7$ | 82.4 |
| HSV-2 | 0.5 | 08 | 5.1E+07 | 6.2E+07 | 5.65E+07 | $5.65 \times 10^7$ | 66.1 |
| HSV-2 | 0.5 | 39 | 5.0E+05 | 7.0E+05 | 6.00E+05 | $6.00 \times 10^5$ | 0.7 |
| HSV-2 | 0.5 | 41 | 3.0E+05 | 7.0E+05 | 5.00E+05 | $5.00 \times 10^5$ | 0.6 |
| HSV-1 | 0.5 | none | 6.0E+07 | 7.6E+07 | 6.80E+07 | $6.80 \times 10^7$ | 100.0 |
| HSV-1 | 0.5 | 01 | 1.2E+08 | 1.2E+08 | 1.20E+08 | $1.20 \times 10^8$ | 176.5 |
| HSV-1 | 0.5 | 03 | 1.3E+08 | 1.7E+08 | 1.50E+08 | $1.50 \times 10^8$ | 220.6 |
| HSV-1 | 0.5 | 07 | 8.9E+07 | 9.5E+07 | 9.20E+07 | $9.20 \times 10^7$ | 135.3 |
| HSV-1 | 0.5 | 08 | 9.0E+07 | 1.2E+08 | 1.05E+08 | $1.05 \times 10^8$ | 154.4 |
| HSV-1 | 0.5 | 09 | 1.5E+08 | 1.8E+08 | 1.65E+08 | $1.64 \times 10^8$ | 241.2 |
| HSV-1 | 0.5 | 35 | 1.7E+07 | 2.0E+07 | 1.85E+07 | $1.85 \times 10^7$ | 27.2 |
| HSV-1 | 0.5 | 37 | 3.5E+07 | 4.7E+07 | 4.10E+07 | $4.10 \times 10^7$ | 60.3 |
| HSV-1 | 0.5 | 38 | 5.7E+06 | 7.1E+06 | 6.40E+06 | $6.40 \times 10^8$ | 9.4 |
| HSV-1 | 0.5 | 40 | 1.7E+09 | 2.1E+09 | 1.86E+09 | $1.86 \times 10^9$ | 2735.3 |
| HSV-1 | 0.05 | none | 2.8E+08 | 3.3E+08 | 3.05E+08 | $3.05 \times 10^8$ | 100.0 |
| HSV-1 | 0.05 | 03 | 3.5E+08 | 4.7E+08 | 4.10E+08 | $4.10 \times 10^8$ | 134.4 |
| HSV-1 | 0.05 | 07 | 2.6E+08 | 3.2E+08 | 2.90E+08 | $2.90 \times 10^8$ | 95.1 |
| HSV-1 | 0.05 | 08 | 3.0E+08 | 4.3E+08 | 3.65E+08 | $3.65 \times 10^8$ | 119.7 |
| HSV-1 | 0.05 | 09 | 3.5E+08 | 3.7E+08 | 3.60E+08 | $3.60 \times 10^8$ | 118.0 |
| HSV-1 | 0.05 | 35 | 4.2E+05 | 6.0E+05 | 5.10E+05 | $5.10 \times 10^5$ | 0.2 |
| HSV-1 | 0.05 | 37 | 2.9E+06 | 3.2E+06 | 3.05E+06 | $3.05 \times 10^6$ | 1.0 |
| HSV-1 | 0.05 | 38 | 2.5E+05 | 3.9E+05 | 3.20E+05 | $3.20 \times 10^5$ | 0.1 |
| HSV-1 | 2.5 | none | 1.5E+08 | 2.5E+08 | 2.00E+08 | $2.00 \times 10^8$ | 100.0 |
| HSV-1 | 2.5 | 01 | 4.0E+08 | 7.1E+08 | 5.55E+08 | $5.55 \times 10^8$ | 277.5 |
| HSV-1 | 2.5 | 02 | 6.2E+08 | 7.6E+08 | 6.90E+08 | $6.90 \times 10^8$ | 345.0 |
| HSV-1 | 2.5 | 03 | 4.0E+08 | 4.3E+08 | 4.15E+08 | $4.15 \times 10^8$ | 207.5 |
| HSV-1 | 2.5 | 04 | 5.0E+08 | 6.1E+08 | 5.55E+08 | $5.55 \times 10^8$ | 277.5 |
| HSV-1 | 2.5 | 06 | 5.4E+08 | 6.1E+08 | 5.75E+08 | $5.75 \times 10^8$ | 287.5 |
| HSV-1 | 2.5 | 07 | 2.9E+08 | 4.1E+08 | 3.50E+08 | $3.50 \times 10^8$ | 175.0 |
| HSV-1 | 0.25 | none | 7.7E+07 | 8.4E+07 | 8.05E+07 | $8.05 \times 10^7$ | 100.0 |
| HSV-1 | 0.25 | 01 | 6.5E+07 | 7.0E+07 | 6.75E+07 | $6.75 \times 10^7$ | 83.9 |
| HSV-1 | 0.25 | 02 | 5.9E+07 | 7.0E+07 | 6.45E+07 | $6.45 \times 10^7$ | 80.1 |
| HSV-1 | 0.25 | 03 | 5.4E+07 | 6.4E+07 | 5.90E+07 | $5.90 \times 10^7$ | 73.3 |
| HSV-1 | 0.25 | 04 | 5.2E+07 | 7.1E+07 | 6.15E+07 | $6.15 \times 10^7$ | 76.4 |
| HSV-1 | 0.25 | 06 | 6.7E+07 | 7.2E+07 | 6.95E+07 | $6.95 \times 10^7$ | 86.3 |
| HSV-1 | 0.25 | 07 | 2.1E+07 | 4.3E+07 | 3.20E+07 | $3.20 \times 10^7$ | 39.8 |
| HSV-2 | 1.5 | none | 1.3E+08 | 1.7E+08 | 1.48E+08 | $1.48 \times 10^8$ | 100.0 |

TABLE 2-continued

| Virus Type | MOI | Oligo. | Yield 1 | Yield 2 | Average | | % of control |
|---|---|---|---|---|---|---|---|
| HSV-2 | 1.5 | 01 | 5.9E+07 | 5.8E+07 | 5.85E+07 | $5.85 \times 10^7$ | 39.5 |
| HSV-2 | 1.5 | 02 | 5.3E+07 | 6.4E+07 | 5.85E+07 | $5.85 \times 10^7$ | 39.5 |
| HSV-2 | 1.5 | 03 | 1.1E+08 | 1.2E+08 | 1.15E+08 | $1.15 \times 10^8$ | 77.7 |
| HSV-2 | 1.5 | 04 | 1.3E+08 | 1.3E+08 | 1.28E+08 | $1.28 \times 10^8$ | 86.5 |
| HSV-2 | 1.5 | 06 | 1.1E+08 | 1.2E+08 | 1.12E+08 | $1.12 \times 10^8$ | 75.7 |
| HSV-2 | 1.5 | 07 | 5.0E+07 | 5.4E+07 | 5.20E+07 | $5.20 \times 10^7$ | 35.1 |
| HSV-2 | 1.5 | 08 | 8.7E+07 | | 8.70E+07 | $8.70 \times 10^7$ | 58.8 |
| HSV-2 | 0.15 | none | 8.0E+07 | 8.4E+07 | 8.20E+07 | $8.20 \times 10^7$ | 100.0 |
| HSV-2 | 0.15 | 01 | 2.8E+07 | 3.1E+07 | 2.95E+07 | $2.95 \times 10^7$ | 36.0 |
| HSV-2 | 0.15 | 02 | 7.3E+07 | 8.5E+07 | 7.90E+07 | $7.90 \times 10^7$ | 96.3 |
| HSV-2 | 0.15 | 03 | 4.4E+07 | 5.0E+07 | 4.70E+07 | $4.70 \times 10^7$ | 57.3 |
| HSV-2 | 0.15 | 04 | 6.7E+07 | 7.2E+07 | 6.95E+07 | $6.95 \times 10^7$ | 84.8 |
| HSV-2 | 0.15 | 06 | 4.4E+07 | 4.8E+07 | 4.60E+07 | $4.60 \times 10^7$ | 56.1 |
| HSV-2 | 0.15 | 07 | 5.0E+07 | 5.4E+07 | 5.20E+07 | $5.20 \times 10^7$ | 63.4 |
| HSV-2 | 0.15 | 08 | 4.0E+07 | 4.1E+07 | 4.05E+07 | $4.05 \times 10^7$ | 49.4 |

The following data were collected in a similar fashion except that the cells were pre-exposed to oligonucleotide for 5 hours rather than 18 hours. In some cases, as indicated, higher oligonucleotide concentrations were employed.

| Virus Type | MOI | Oligo. | Yield 1 | Yield 2 | Average | | % of control | |
|---|---|---|---|---|---|---|---|---|
| HSV-1 | 0.5 | none | 6.1E+08 | 6.8E+08 | 6.45E+08 | $6.45 \times 10^8$ | 100.0 | |
| HSV-1 | 0.5 | 01 | 6.4E+08 | 7.4E+08 | 6.90E+08 | $6.90 \times 10^8$ | 107.0 | |
| HSV-1 | 0.5 | 02 | 6.2E+08 | 6.5E+08 | 6.35E+08 | $6.35 \times 10^8$ | 98.4 | 8 μM |
| HSV-1 | 0.5 | 03 | 7.9E+08 | 9.0E+08 | 8.45E+08 | $8.45 \times 10^8$ | 131.0 | 11 μM |
| HSV-1 | 0.5 | 06 | 5.7E+08 | 7.0E+08 | 6.35E+08 | $6.35 \times 10^8$ | 98.4 | |
| HSV-1 | 0.5 | 07 | 7.0E+08 | 8.0E+08 | 7.50E+08 | $7.50 \times 10^8$ | 116.3 | |
| HSV-1 | 0.5 | 08 | 6.9E+08 | 8.9E+08 | 7.90E+08 | $7.90 \times 10^8$ | 122.5 | 15 μM |
| HSV-1 | 0.5 | 09 | 6.6E+08 | 8.1E+08 | 7.35E+08 | $7.35 \times 10^8$ | 114.5 | |
| HSV-1 | 0.5 | 35 | 4.0E+05 | 5.0E+05 | 4.50E+05 | $4.50 \times 10^5$ | <0.1 | |
| HSV-1 | 0.5 | 37 | 1.8E+06 | | 1.8E+06 | $1.8 \times 10^6$ | 0.3 | |
| HSV-1 | 0.5 | 38 | 3.2E+06 | 3.8E+06 | 3.50E+06 | $3.50 \times 10^6$ | 0.5 | |
| HSV-1 | 0.05 | none | 6.7E+08 | 8.6E+08 | 7.65E+08 | $7.65 \times 10^8$ | 100.0 | |
| HSV-1 | 0.05 | 03 | 7.8E+07 | 9.0E+07 | 8.40E+07 | $8.40 \times 10^7$ | 11.0 | 11 μM |
| HSV-1 | 0.05 | 06 | 7.6E+07 | 7.7E+07 | 7.65E+07 | $7.65 \times 10^7$ | 10.0 | |
| HSV-1 | 0.05 | 07 | 8.4E+07 | 8.4E+07 | 8.40E+07 | $8.40 \times 10^7$ | 11.0 | |
| HSV-1 | 0.05 | 08 | 6.5E+07 | 8.3E+07 | 7.40E+07 | $7.40 \times 10^7$ | 9.7 | 15 μM |
| HSV-1 | 0.05 | 09 | 3.8E+07 | 4.5E+07 | 4.15E+07 | $4.15 \times 10^7$ | 5.4 | |
| HSV-1 | 0.05 | 35 | 4.5E+04 | 4.8E+04 | 4.65E+04 | $4.65 \times 10^4$ | <0.01 | |
| HSV-1 | 0.05 | 37 | 9.5E+04 | 1.0E+05 | 9.95E+04 | $9.95 \times 10^4$ | 0.01 | |
| HSV-1 | 0.05 | 38 | 2.3E+04 | 2.7E+04 | 2.50E+04 | $2.50 \times 10^4$ | <0.01 | |
| HSV-2 | 0.5 | none | 5.3E+07 | 6.3E+07 | 5.80E+07 | $5.80 \times 10^7$ | 100.0 | |
| HSV-2 | 0.5 | 07 | 2.8E+07 | 3.0E+07 | 2.90E+07 | $2.90 \times 10^7$ | 50.0 | |
| HSV-2 | 0.5 | 38 | 6.5E+06 | 7.1E+06 | 6.80E+06 | $6.80 \times 10^6$ | 11.7 | |
| HSV-2 | 0.05 | none | 4.3E+07 | 4.3E+07 | 4.30E+07 | $4.30 \times 10^7$ | 100.0 | |
| HSV-2 | 0.05 | 07 | 1.6E+07 | 1.8E+07 | 1.70E+07 | $1.70 \times 10^7$ | 39.5 | |
| HSV-2 | 0.05 | 38 | 6.7E+04 | 8.0E+04 | 7.35E+04 | $7.35 \times 10^4$ | 0.2 | |

The following data were collected in a similar fashion except that the cells were pre-exposed to oligonucleotide for 5 hours rather than 18 hours. In some cases, as indicated, higher oligonucleotide concentrations were employed.

| Virus Type | MOI | Oligo. | Yield 1 | Yield 2 | Average | |
|---|---|---|---|---|---|---|
| HSV-1 | 0.5 | none | 6.1E+08 | 6.8E+08 | 6.45E+08 | |
| HSV-1 | 0.5 | 01 | 6.4E+08 | 7.4E+08 | 6.90E+08 | |
| HSV-1 | 0.5 | 02 | 6.2E+08 | 6.5E+08 | 6.35E+08 | 8 μM |
| HSV-1 | 0.5 | 03 | 7.9E+08 | 9.0E+08 | 8.45E+08 | 11 μM |
| HSV-1 | 0.5 | 06 | 5.7E+08 | 7.0E+08 | 6.35E+08 | |
| HSV-1 | 0.5 | 07 | 7.0E+08 | 8.0E+08 | 7.50E+08 | |
| HSV-1 | 0.5 | 08 | 6.9E+08 | 8.9E+08 | 7.90E+08 | 15 μM |
| HSV-1 | 0.5 | 09 | 6.6E+08 | 8.1E+08 | 7.35E+08 | |
| HSV-1 | 0.5 | 35 | 4.0E+05 | 5.0E+05 | 4.50E+05 | |
| HSV-1 | 0.5 | 37 | 1.8E+06 | | 1.8E+06 | |
| HSV-1 | 0.5 | 38 | 3.2E+06 | 3.8E+06 | 3.50E+06 | |
| HSV-1 | 0.05 | none | 6.7E+08 | 8.6E+08 | 7.65E+08 | |
| HSV-1 | 0.05 | 03 | 7.8E+07 | 9.0E+07 | 8.40E+07 | 11 μM |
| HSV-1 | 0.05 | 06 | 7.6E+07 | 7.7E+07 | 7.65E+07 | |
| HSV-1 | 0.05 | 07 | 8.4E+07 | 8.4E+07 | 8.40E+07 | |
| HSV-1 | 0.05 | 08 | 6.5E+07 | 8.3E+07 | 7.40E+07 | 15 μM |
| HSV-1 | 0.05 | 09 | 3.8E+07 | 4.5E+07 | 4.15E+07 | |
| HSV-1 | 0.05 | 35 | 4.5E+04 | 4.8E+04 | 4.65E+04 | |
| HSV-1 | 0.05 | 37 | 9.5E+04 | 1.0E+05 | 9.95E+04 | |
| HSV-1 | 0.05 | 38 | 2.3E+04 | 2.7E+04 | 2.50E+04 | |
| HSV-2 | 0.5 | none | 5.3E+07 | 6.3E+07 | 5.80E+07 | |
| HSV-2 | 0.5 | 07 | 2.8E+07 | 3.0E+07 | 2.90E+07 | |
| HSV-2 | 0.5 | 38 | 6.5E+06 | 7.1E+06 | 6.80E+06 | |
| HSV-2 | 0.05 | none | 4.3E+07 | 4.3E+07 | 4.30E+07 | |
| HSV-2 | 0.05 | 07 | 1.6E+07 | 1.8E+07 | 1.70E+07 | |
| HSV-2 | 0.05 | 38 | 6.7E+04 | 8.0E+04 | 7.35E+04 | |

For the foregoing, it is readily apparent that substantial reductions in virus replication can result from the application of oligonucleotides in accordance with this invention.

What is claimed is:

1. An oligonucleotide or an oligonucleotide having at least one phosphorothioate internucleotide bond consisting essentially of 15 to 30 nucleotides in length, which contains the CAT sequence and which is specifically hybridizable under stringent conditions to the translation initiation region of an open reading frame of a herpes simplex virus type 1 gene selected from the group consisting of UL13, UL39, and UL40, and which is capable of reducing viral yield at least three-fold.

2. A pharmaceutical composition comprising an oligonucleotide of claim 1 and a pharmaceutically acceptable carrier.

3. An oligonucleotide or an oligonucleotide having at least one phosphorothioate internucleotide bond consisting essentially of a sequence selected from the group consisting of

| | | | | | | |
|---|---|---|---|---|---|---|
| GTC | CGC | GTC | CAT | GTC | GGC. | |
| GGA | CTC | ATC | CAT | CCT | TCG | GCC, |
| GCG | GCT | GGC | CAT | TTC | AAC | AGA, |
| CGC | GGA | ATC | CAT | GGC | AGC | AGG, |
| ACC | GAG | GTC | CAT | GTC | GTA | CGC, |
| GGA | CTC | ATC | CAT | CCG | TCC | GCC, |
| GCC | GAG | GTC | CAT | GTC | GTA | CGC, |
| GCG | GTT | GGC | CAT | TGG | AAC | CAA, AND |
| GGC | GGG | ATC | CAT | GGC | GAT | ATG. |

4. A pharmaceutical composition comprising an oligonucleotide of claim 3 and a pharmaceutically acceptable carrier.

* * * * *

UNITED STATES PATENT AND TRADEMARK OFFICE
CERTIFICATE OF CORRECTION

PATENT NO. : 5,248,670
DATED : Sept. 28, 1993
INVENTOR(S) : Kenneth G. Draper, et al It is certified that error appears in the above-indentified patent and that said Letters Patent is hereby corrected as shown below:

```
Column 2, line 1,  delete "was" and insert -- was --.
Column 3, line 65, delete "HSV 1" and insert -- HSV-1 --.
Column 5, line 20, delete "gen" and insert -- gene --.
Column 9, line 8,  delete "2972" and insert -- 2792 --.
Column 9, line 43, delete "gen." and insert -- Gen. --.
Cols. 13 and 14, Table 2, line 23, delete
```

HSV-1  0.5  09  1.5E+08  1.8E+08  1.65E+08  $1.64 \times 10^8$  241.2 and insert

HSV-1  0.5  09  1.5E+08  1.8E+08  1.64E+08  $1.64 \times 10^8$  241.2

Table 2, line 26, delete

HSV-1  0.5  38  5.75E+06  7.1E+06  6.40E+06  $6.40 \times 10^8$  9.4 and insert

HSV-1  0.5  38  5.75E+06  7.1E+06  6.40E+06  $6.40 \times 10^6$  9.4

Table 2, line 23, delete

HSV-1  0.5  03  7.9E+08  9.0E+08  8.45E+08  8.45X108  131.0  $11\mu M$ and insert HSV-1  0.5  03  7.9E+08  9.0E+08  8.45E+08  $8.45 \times 10^8$  131.0  $11\mu M$

UNITED STATES PATENT AND TRADEMARK OFFICE
CERTIFICATE OF CORRECTION

PATENT NO. : 5,248,670
DATED : Sept. 28, 1993
INVENTOR(S) : Kenneth G. Draper, et al It is certified that error appears in the above-indentified patent and that said Letters Patent is hereby corrected as shown below:

Column 17, line 1, delete "For" and insert --From--

Signed and Sealed this

Twelfth Day of April, 1994

Attest:

BRUCE LEHMAN

*Attesting Officer*  *Commissioner of Patents and Trademarks*